(12) United States Patent
Chiorini

(10) Patent No.: US 10,166,299 B2
(45) Date of Patent: Jan. 1, 2019

(54) AAV MEDIATED AQUAPORIN GENE TRANSFER TO TREAT SJOGREN'S SYNDROME

(71) Applicant: THE UNITED STATES OF AMERICA, AS REPRESENTED BY THE SECRETARY, DEPT. OF HEALTH AND HUMAN SERVICES, Washington, DC (US)

(72) Inventor: John Chiorini, Dayton, MD (US)

(73) Assignee: THE UNITED STATES OF AMERICA AS REPRESENTED BY THE SECRETARY DEPT. OF HEALTH AND HUMAN SERVICES NATIONAL INSTITUTES OF HEALTH, Washington, DC (US)

(*) Notice: Subject to any disclaimer, the term of this patent is extended or adjusted under 35 U.S.C. 154(b) by 0 days.

(21) Appl. No.: 14/423,774

(22) PCT Filed: Aug. 30, 2013

(86) PCT No.: PCT/US2013/057632
§ 371 (c)(1),
(2) Date: Feb. 25, 2015

(87) PCT Pub. No.: WO2014/036468
PCT Pub. Date: Mar. 6, 2014

(65) Prior Publication Data
US 2015/0203553 A1 Jul. 23, 2015

Related U.S. Application Data

(60) Provisional application No. 61/695,753, filed on Aug. 31, 2012.

(51) Int. Cl.
*A61K 48/00* (2006.01)
*C12N 15/86* (2006.01)
*C07K 14/705* (2006.01)
*C07K 14/47* (2006.01)
*A61K 38/17* (2006.01)

(52) U.S. Cl.
CPC .......... *A61K 48/005* (2013.01); *A61K 38/177* (2013.01); *A61K 48/00* (2013.01); *C07K 14/47* (2013.01); *C07K 14/705* (2013.01); *C12N 15/86* (2013.01); *C12N 2750/14143* (2013.01)

(58) Field of Classification Search
CPC .... A61K 48/005; A61K 48/00; A61K 38/177; C07K 14/47; C07K 14/705; C12N 15/86; C12N 2750/14143
USPC ........... 514/44 R; 435/320.1, 455; 424/199.1
See application file for complete search history.

(56) References Cited

U.S. PATENT DOCUMENTS

| 9,511,103 B2 | 12/2016 | Chiorini et al. |
| 2002/0114814 A1 | 8/2002 | Gray et al. |
| 2003/0007968 A1 | 1/2003 | Larsen et al. |
| 2005/0107318 A1 | 5/2005 | Wadsworth et al. |
| 2007/0253973 A1 | 11/2007 | Rosen et al. |
| 2008/0293618 A1 | 11/2008 | Ulrich et al. |
| 2009/0186097 A1 | 7/2009 | Ayares |
| 2010/0166756 A1 | 7/2010 | Cohen et al. |
| 2010/0166774 A1 | 7/2010 | Dalii et al. |
| 2014/0147418 A1 | 5/2014 | Chiorini et al. |
| 2017/0143779 A1 | 5/2017 | Chiorini et al. |

FOREIGN PATENT DOCUMENTS

| WO | WO 99/64569 | 12/1999 |
| WO | WO 03/014318 | 2/2003 |
| WO | WO 2003/030946 | 4/2003 |
| WO | WO 2003/088991 | 10/2003 |
| WO | WO 2004/087196 | 10/2004 |
| WO | WO 2007/016764 | 2/2007 |
| WO | WO 2008/012629 | 1/2008 |
| WO | WO 2013/134931 | * 9/2013 |

OTHER PUBLICATIONS

Delporte et al. (1997) PNAS, vol. 94, 3268-3273.*
Braddon et al. (1998) Human Gene Therapy, vol. 9, 2777-2785.*
Preston and Agre (1991) PNAS, vol. 88, 11110-11114.*
Motegi et al. (2005) Lab. Invest., vol. 85, 243-353.*
UniprotKB/Swiss-Prot Accession No. Q02013 AQP1_MOUSE, integrated into database on Jun. 1, 1994.*
Baum, B., et al., "Transfer of the AQP1 cDNA for the correction of radiation-induced salivary hypofunction", Biochimica Et Biophysica Acta (BBA) Biomembranes, vol. 1758, No. 8, Aug. 1, 2006 (Aug. 1, 2006), pp. 1071-1077, XP027916090.
Baum, Bruce J., et al., "Advances in vector-mediated gene transfer," Immunology Letters, vol. 90, No. 2-3, Dec. 15, 2003 (Dec. 15, 2003), pp. 145-149, XP002716298.
Braddon, Virginia R., et al., "Adenoassociated virus-mediated transfer of a functional water channel into salivary epithelial cells in vitro and in vivo," Human Gene Therapy, vol. 9, No. 18, Dec. 10, 1998 (Dec. 10, 1998), pp. 2777-2785, XP002716297.
Delporte, Christine, et al., "Increased fluid secretion after adenoviral-mediated transfer of the aquaporin-1 cDNA to irradiated rat salivary glands," Proceedings of the National Academy of Sciences -, vol. 94, No. 7, Apr. 1997 (Jan. 1, 1997), pp. 3268-3273~ XP002148673.
Evans, Christopher H., et al., "Gene therapy of the rheumatic diseases: 1998 to 2008.", Arthritis Research & Therapy, vol. 11, No. 1, 2009, pp. 209-220, XP002716300.

(Continued)

*Primary Examiner* — Anne Marie S Wehbe
(74) *Attorney, Agent, or Firm* — Fox Rothschild LLP

(57) ABSTRACT

The invention relates to a gene transfer-based method to protect a subject from Sjogren's syndrome. The method comprises administering to the subject an AAV virion comprising an AAV vector that encodes aquaporin-1 (AQP-1) protein. Also provided are AQP-1 proteins and nucleic acid molecules that encode such proteins. Also provided are AAV vectors and AAV virions that encode an AQP-1 protein.

8 Claims, 7 Drawing Sheets

Specification includes a Sequence Listing.

(56) References Cited

OTHER PUBLICATIONS

Hayashi, Toshiharu, "Dysfunction of lacrimal and salivary glands in Sjogren's syndrome: nonimmunologic injury in preinflammatory phase and mouse model.", Journal of Biomedicine & Biotechnology, vol. 2011, 407031, 2011, pp. 1-15, XP002716299.
Kok, M.R., et al., "Use of localised gene transfer to develop new treatment strategies for the salivary component of Sjogren's syndrome," Annals of the Rheumatic Diseases, vol. 62, No. 11, Nov. 1, 2003 (Nov. 1, 2013), pp. 1038-1046, XP009144242.
Mariette, Xavier, et al., "Pathogenesis of Sjogren's syndrome and therapeutic consequences," Current Opinion in Rheumatology, vol. 22, No. 5, Sep. 1, 2010 (Sep. 1, 2010), pp. 471-477, XP009174115.
Shan, Z., et al., "Increased fluid secretion after adenoviral-mediated transfer of the human aquaporin-1 cDNA to irradiated miniature pig parotid glands", Molecular Therapy, vol. 11, No. 3, Mar. 1, 2005 (Mar. 1, 2005), pp. 444-451, XP004757252.
Soyfoo, Muhammad, et al., "Modified aquaporin 5 expression and distribution in submandibular glands from NOD mice displaying autoimmune exocrinopathy,", Arthritis & Rheumatism, vol. 56, No. 8, Aug. 2007 (Aug. 2007), pp. 2566-2574, XP002716296.
Steinfeld, Serge, et al., "Abnormal distribution of aquaporin-5 water channel protein in salivary glands from Sjogren's syndrome patients," Laboratory Investigation, vol. 81, No. 2, Feb. 2001 (Deb. 2001), pp. 143-148, XP002716295.
Xiao, L., et al., "Dendrobium candidum extract increases the expression of aquaporin-5 in labial glands from patients with Sjogren's syndrome", Phytomedicine, vol. 18, No. 2-3, Jan. 15, 2011 (Jan. 15, 2011), pp. 194-198, XP027587196.
International Search Report and Written Opinion for International (PCT) Patent Application No. PCT/US13/57632, dated Apr. 9, 2014, 17 pages.
Choi et al. "Long-term, antidiabetogenic effects of GLP-1 gene therapy using a double-stranded, adeno-associated viral vector," Gene Therapy, Feb. 2011, vol. 18, No. 2, pp. 155-163.
Katano et al. "Enhanced transduction of mouse salivary glands with AAV5-based vectors," Gene Therapy, Apr. 2006, vol. 13, No. 7, pp. 594-601.
Official Action for Canada Patent Application No. 2,882,763, dated Dec. 23, 2015 3 pages.
"Correlation does not imply causation," Wikipedia, last modified Oct. 24, 2015, 9 pages [retrieved from: en.wikipedia.org/wiki/Correlation_does_not_imply_causation].
"Definition of protect," Dictionary.com, printed Dec. 10, 2015, 4 pages. [retrieved online from: dictionary.reference.com/browse/protect].
Bouard et al. "Viral vectors: from virology to transgene expression," Br J Pharmacol, 2009, vol. 157, No. 2, pp. 153-165.
Bryan et al., 2013, http://www.elsevierblogs.com/currentcommentsl?p=962, "Implications of protein fold switching," p. 1-4.
Chattopadhyay et al., "Effect of single amino acid mutations in the conserved GDNQ motif of L protein of Rinderpest virus on RNA synthesis in vitro and in vivo," 2004, Virus Research, vol. 99, p. 139-145.
Giovanni Di Pasquale et al: "Sustained Exendin-4 Secretion through Gene Therapy Targeting Salivary Glands in Two Different Rodent Models of Obesity/Type 2 Diabetes". PLOS One, vol. 7, No. 7, Jul. 13, 2012 (Jul. 13, 2012), p. e40074, XP55143570.
Gupta "Glucagon-like peptide-1 analogues: an overview," 2013, Indian Journal of Endocrinology and Metabolism, 17(3), p. 413-421.
Lee et al. "Sjogren's syndrome: An old tale with a new twist," Arch Immunol Ther Exp, 2009, vol. 57, No. 1, pp. 1-16.
Pandey "Functional Effects of Proline Substitutions into Sindbis Virus E2 Transmebrane Domain," 2007, Abstracts, 59th Southeast regional Meeting of the American Chemical Society, Greenville, SC, United States, GEN-671, Publisher: American Chemical Society, Washington D.C.
Ramos-Casals, M. et al., "Emerging biological therapies in primary Sjogren's syndrome," Rheumatology (Oxford), vol. 46, No. 9, Sep. 2007 pp. 1389-1396, XP002729681.
Rowzee, Anne M., et al, "'Glucagon-Like Peptide-I Gene Therapy," Exp Diabetes Res., Jun. 20, 2011, vol. 2011, pp. 1-5.
Samuni et al. "Gene Delivery in salivary glands: from the bench to the clinic," Biochim Biophys Acta, 2011, vol. 1812, No. 11, pp. 1515-1521.
Skolnick et al., "From genes to protein structure and function: novel applications of computational approaches in the genomic era," 2000, Trends in Biotech, vol. 18, p. 34-39.
Smallwood et al., "Different Substitutions at Conserved Amino Acids in Domains II and III in the Sendai L RNA Polymerase Protein Inactivate Viral RNA Synthesis," 2002 Virology, vol. 304, p. 135-145.
Tomasinsig et al., "The Cathelicidins—Structure, Function and Evolution," 2005, Current Protein and Peptide Science, vol. 6, p. 23-34.
Vosters, Jelle, L., et al., "Local expression of tumor necrosis factor-receptor I: immunoglobulin G can induce salivary gland dysfunction in a murine model of Sjogren's syndrome," Arthritis Research and Therapy, Biomed Central, London, GB, vol . 11, No. 6, Dec. 14, 2009, p. R189, XP021070714.
Xue-Wu Xu et al: "Human signal peptide had advantage over mouse in secretory expression". Histochemistry and Cell Biology. Springer, Berlin. DE, vol. 132, No. 2, Apr. 29, 2009 (Apr. 29, 2009). pp. 239-246.
Official Action for Australia Patent Appication No. 2013308470, dated Sep. 28, 2016 3 pages.
Notice of Acceptance for Australia Patent Application No. 2013308470, dated Apr. 5, 2017 3 pages.
Official Action for Canada Patent Application No. 2,882,763, dated Nov. 8, 2016 4 pages.
Finan et al. "Emerging opportunities for the treatment of metabolic diseases: Glucagon-like peptide-1 based multi-agonists," Molecular and Cellular Endocrinology, 2015, vol. 418, pp. 42-54.
Troke et al. "The future role of gut hormones in the treatment of obesity," Therapeutic Advances in Chronic Disease, 2014, vol. 5, No. 1, pp. 4-14.
Official Action for Canada Patent Application No. 2,882,763, dated Oct. 26, 2017 3 pages.

* cited by examiner

SEQUENCE LISTING

<160> NUMBER OF SEQ ID NOS: 19

<210> SEQ ID NO 1
<211> LENGTH: 810
<212> TYPE: DNA
<213> ORGANISM: Homo sapiens

<400> SEQUENCE: 1

```
atggccagcg agttcaagaa gaagctcttc tggagggcag tggtggccga gttcctggcc      60
acgaccctct ttgtcttcat cagcatcggt tctgccctgg gcttcaaata cccggtgggg     120
aacaaccaga cggcggtcca ggacaacgtg aaggtgtcgc tggccttcgg gctgagcatc     180
gccacgctgg cgcagagtgt gggccacatc agcggcgccc acctcaaccc ggctgtcaca     240
ctggggctgc tgctcagctg ccagatcagc atcttccgtg ccctcatgta catcatcgcc     300
cagtgcgtgg gggccatcgt cgccaccgcc atcctctcag gcatcacctc ctccctgact     360
gggaactcgc ttggccgcaa tgacctggct gatggtgtga actcgggcca gggcctgggc     420
atcgagatca tcgggaccct ccagctggtg ctatgcgtgc tggctactac cgaccggagg     480
cgccgtgacc ttggtggctc agcccccctt gccatcggcc tctctgtagc ccttggacac     540
ctcctggcta ttgactacac tggctgtggg attaaccctc ctcggtcctt tggctccgcg     600
gtgatcacac acaacttcag caaccactgg attttctggg tggggccatt catcggggga     660
gccctggctg tactcatcta cgacttcatc ctggcccac gcagcagtga cctcacagac     720
cgcgtgaagg tgtggaccag cggccaggtg gaggagtatg acctggatgc cgacgacatc     780
aactccaggg tggagatgaa gcccaaatag                                      810
```

<210> SEQ ID NO 2
<211> LENGTH: 269
<212> TYPE: PRT
<213> ORGANISM: Homo sapiens

<400> SEQUENCE: 2

```
Met Ala Ser Glu Phe Lys Lys Lys Leu Phe Trp Arg Ala Val Val Ala
1               5                   10                  15

Glu Phe Leu Ala Thr Thr Leu Phe Val Phe Ile Ser Ile Gly Ser Ala
            20                  25                  30

Leu Gly Phe Lys Tyr Pro Val Gly Asn Asn Gln Thr Ala Val Gln Asp
        35                  40                  45

Asn Val Lys Val Ser Leu Ala Phe Gly Leu Ser Ile Ala Thr Leu Ala
```

```
                50              55              60
Gln Ser Val Gly His Ile Ser Gly Ala His Leu Asn Pro Ala Val Thr
 65                  70                  75                  80

Leu Gly Leu Leu Leu Ser Cys Gln Ile Ser Ile Phe Arg Ala Leu Met
                 85                  90                  95

Tyr Ile Ile Ala Gln Cys Val Gly Ala Ile Val Ala Thr Ala Ile Leu
                100                 105                 110

Ser Gly Ile Thr Ser Ser Leu Thr Gly Asn Ser Leu Gly Arg Asn Asp
            115                 120                 125

Leu Ala Asp Gly Val Asn Ser Gly Gln Gly Leu Gly Ile Glu Ile Ile
        130                 135                 140

Gly Thr Leu Gln Leu Val Leu Cys Val Leu Ala Thr Thr Asp Arg Arg
145                 150                 155                 160

Arg Arg Asp Leu Gly Gly Ser Ala Pro Leu Ala Ile Gly Leu Ser Val
                165                 170                 175

Ala Leu Gly His Leu Leu Ala Ile Asp Tyr Thr Gly Cys Gly Ile Asn
            180                 185                 190

Pro Ala Arg Ser Phe Gly Ser Ala Val Ile Thr His Asn Phe Ser Asn
        195                 200                 205

His Trp Ile Phe Trp Val Gly Pro Phe Ile Gly Gly Ala Leu Ala Val
210                 215                 220

Leu Ile Tyr Asp Phe Ile Leu Ala Pro Arg Ser Ser Asp Leu Thr Asp
225                 230                 235                 240

Arg Val Lys Val Trp Thr Ser Gly Gln Val Glu Glu Tyr Asp Leu Asp
                245                 250                 255

Ala Asp Asp Ile Asn Ser Arg Val Glu Met Lys Pro Lys
            260                 265
```

<210> SEQ ID NO 3
<211> LENGTH: 810
<212> TYPE: DNA
<213> ORGANISM: Homo sapiens

<400> SEQUENCE: 3

```
ctatttgggc ttcatctcca ccctggagtt gatgtcgtcg gcatccaggt catactcctc      60
cacctggccg ctggtccaca ccttcacgcg gtctgtgagg tcactgctgc gtggggccag     120
gatgaagtcg tagatgagta cagccagggc tcccccgatg aatggcccca cccagaaaat     180
ccagtggttg ctgaagttgt gtgtgatcac cgcggagcca aaggaccgag cagggttaat     240
cccacagcca gtgtagtcaa tagccaggag gtgtccaagg gctacagaga ggccgatggc     300
aagggggggct gagccaccaa ggtcacggcg cctccggtcg gtagtagcca gcacgcatag     360
caccagctgg agggtcccga tgatctcgat gcccaggccc tggcccgagt tcacaccatc     420
agccaggtca ttgcggccaa gcgagttccc agtcagggag gaggtgatgc ctgagaggat     480
ggcggtggcg acgatggccc ccacgcactg ggcgatgatg tacatgaggg cacggaagat     540
gctgatctgg cagctgagca gcagccccag tgtgacagcc gggttgaggt gggcgccgct     600
gatgtggccc acactctgcg ccagcgtggc gatgctcagc cgaaggcca gcgacacctt     660
cacgttgtcc tggaccgccg tctggttgtt ccccaccggg tatttgaagc ccagggcaga     720
accgatgctg atgaagacaa agagggtcgt ggccaggaac tcggccacca ctgccctcca     780
gaagagcttc ttcttgaact cgctggccat                                       810
```

<210> SEQ ID NO 4

<211> LENGTH: 561
<212> TYPE: DNA
<213> ORGANISM: Homo sapiens

<400> SEQUENCE: 4

```
atgcctgggg ctcgccccctt gcctctggtc ttggtacccc agaatacccct ggcctggatg    60
cagctggatg caaaggcccc agctcacccc aggcctctcc agcttctagg cagagtgggg   120
cctgggtcta ggcagctggc tgatggtgtg aactcgggcc agggcctggg catcgagatc   180
atcgggaccc tccagctggt gctatgcgtg ctggctacta ccgaccggag gcgccgtgac   240
cttggtggct cagccccct tgccatcggc ctctctgtag cccttggaca cctcctggct   300
attgactaca ctggctgtgg gattaaccct gctcggtcct ttggctccgc ggtgatcaca   360
cacaacttca gcaaccactg gattttctgg gtggggccat tcatcggggg agccctggct   420
gtactcatct acgacttcat cctggcccca cgcagcagtg acctcacaga ccgcgtgaag   480
gtgtggacca cggccaggt ggaggagtat gacctggatg ccgacgacat caactccagg   540
gtggagatga agcccaaata g                                              561
```

<210> SEQ ID NO 5
<211> LENGTH: 186
<212> TYPE: PRT
<213> ORGANISM: Homo sapiens

<400> SEQUENCE: 5

```
Met Pro Gly Ala Arg Pro Leu Pro Leu Val Leu Val Pro Gln Asn Thr
  1               5                  10                  15
Leu Ala Trp Met Gln Leu Asp Ala Lys Ala Pro Ala His Pro Arg Pro
             20                  25                  30
Leu Gln Leu Leu Gly Arg Val Gly Pro Gly Ser Arg Gln Leu Ala Asp
         35                  40                  45
Gly Val Asn Ser Gly Gln Gly Leu Gly Ile Glu Ile Ile Gly Thr Leu
     50                  55                  60
Gln Leu Val Leu Cys Val Leu Ala Thr Thr Asp Arg Arg Arg Arg Asp
 65                  70                  75                  80
Leu Gly Gly Ser Ala Pro Leu Ala Ile Gly Leu Ser Val Ala Leu Gly
                 85                  90                  95
His Leu Leu Ala Ile Asp Tyr Thr Gly Cys Gly Ile Asn Pro Ala Arg
            100                 105                 110
Ser Phe Gly Ser Ala Val Ile Thr His Asn Phe Ser Asn His Trp Ile
        115                 120                 125
Phe Trp Val Gly Pro Phe Ile Gly Gly Ala Leu Ala Val Leu Ile Tyr
    130                 135                 140
Asp Phe Ile Leu Ala Pro Arg Ser Ser Asp Leu Thr Asp Arg Val Lys
145                 150                 155                 160
Val Trp Thr Ser Gly Gln Val Glu Glu Tyr Asp Leu Asp Ala Asp Asp
                165                 170                 175
Ile Asn Ser Arg Val Glu Met Lys Pro Lys
            180                 185
```

<210> SEQ ID NO 6
<211> LENGTH: 561
<212> TYPE: DNA
<213> ORGANISM: Homo sapiens

<400> SEQUENCE: 6

```
ctatttgggc ttcatctcca ccctggagtt gatgtcgtcg gcatccaggt catactcctc    60
```

```
cacctggccg ctggtccaca ccttcacgcg gtctgtgagg tcactgctgc gtggggccag      120
gatgaagtcg tagatgagta cagccagggc tcccccgatg aatggcccca cccagaaaat      180
ccagtggttg ctgaagttgt gtgtgatcac cgcggagcca aaggaccgag cagggttaat      240
cccacagcca gtgtagtcaa tagccaggag gtgtccaagg gctacagaga ggccgatggc      300 aagggggct gagccaccaa ggtcacggcg cctccggtcg gtagtagcca gcacgcatag       360
caccagctgg agggtcccga tgatctcgat gcccaggccc tggcccgagt tcacaccatc      420
agccagctgc ctagacccag gccccactct gcctagaagc tggagaggcc tggggtgagc      480
tggggccttt gcatccagct gcatccaggc cagggtattc tggggtacca agaccagagg      540 caagggggcga gccccaggca t                                              561
```

```
<210> SEQ ID NO 7
<211> LENGTH: 657
<212> TYPE: DNA
<213> ORGANISM: Homo sapiens

<400> SEQUENCE: 7
atgttctgga ctttggggta tgaagccgtg tcccctgctg ggccttccca ccttttttgca     60 tctcttctcc taggagtgct cctgaccatc accttcatgc ctggggctcg ccccttgcct    120
ctggtcttgg tacccagaa taccctggcc tggatgcagc tggatgcaaa ggccccagct    180
caccccaggc ctctccagct tctaggcaga gtggggcctg gtctaggca gctggctgat    240 ggtgtgaact cgggccaggg cctgggcatc gagatcatcg gaccctcca gctggtgcta    300 tgcgtgctgg ctactaccga ccggaggcgc cgtgaccttg gtggctcagc ccccttgcc    360 atcggcctct ctgtagccct tggacaccctc ctggctattg actacactgg ctgtgggatt   420
aaccctgctc ggtcctttgg ctccgcggtg atcacacaca acttcagcaa ccactggatt   480
ttctgggtgg ggccattcat cgggggagcc ctggctgtac tcatctacga cttcatcctg   540
gccccacgca gcagtgacct cacagaccgc gtgaaggtgt ggaccagcgg ccaggtggag   600
gagtatgacc tggatgccga cgacatcaac tccagggtgg agatgaagcc caaatag      657
```

```
<210> SEQ ID NO 8
<211> LENGTH: 218
<212> TYPE: PRT
<213> ORGANISM: Homo sapiens

<400> SEQUENCE: 8

Met Phe Trp Thr Phe Gly Tyr Glu Ala Val Ser Pro Ala Gly Pro Ser
1               5                   10                  15

His Leu Phe Ala Ser Leu Leu Gly Val Leu Leu Thr Ile Thr Phe
            20                  25                  30

Met Pro Gly Ala Arg Pro Leu Pro Leu Val Leu Val Pro Gln Asn Thr
        35                  40                  45

Leu Ala Trp Met Gln Leu Asp Ala Lys Ala Pro Ala His Pro Arg Pro
    50                  55                  60

Leu Gln Leu Leu Gly Arg Val Gly Pro Gly Ser Arg Gln Leu Ala Asp
65                  70                  75                  80

Gly Val Asn Ser Gly Gln Gly Leu Gly Ile Glu Ile Ile Gly Thr Leu
                85                  90                  95

Gln Leu Val Leu Cys Val Leu Ala Thr Thr Asp Arg Arg Arg Arg Asp
            100                 105                 110

Leu Gly Gly Ser Ala Pro Leu Ala Ile Gly Leu Ser Val Ala Leu Gly
```

```
                    115                 120                 125
        His Leu Leu Ala Ile Asp Tyr Thr Gly Cys Gly Ile Asn Pro Ala Arg
            130                 135                 140

Ser Phe Gly Ser Ala Val Ile Thr His Asn Phe Ser Asn His Trp Ile
        145                 150                 155                 160

Phe Trp Val Gly Pro Phe Ile Gly Gly Ala Leu Ala Val Leu Ile Tyr
                        165                 170                 175

Asp Phe Ile Leu Ala Pro Arg Ser Ser Asp Leu Thr Asp Arg Val Lys
                    180                 185                 190

Val Trp Thr Ser Gly Gln Val Glu Glu Tyr Asp Leu Asp Ala Asp Asp
                195                 200                 205

Ile Asn Ser Arg Val Glu Met Lys Pro Lys
            210                 215
```

<210> SEQ ID NO 9
<211> LENGTH: 657
<212> TYPE: DNA
<213> ORGANISM: Homo sapiens

<400> SEQUENCE: 9

```
ctatttgggc ttcatctcca ccctggagtt gatgtcgtcg gcatccaggt catactcctc    60
cacctggccg ctggtccaca ccttcacgcg gtctgtgagg tcactgctgc gtggggccag   120
gatgaagtcg tagatgagta cagccagggc tcccccgatg aatggcccca cccagaaaat   180
ccagtggttg ctgaagttgt gtgtgatcac cgcggagcca aggaccgagc agggttaat    240
cccacagcca gtgtagtcaa tagccaggag gtgtccaagg ctacagaga ggccgatggc    300
aagggggggct gagccaccaa ggtcacggcg cctccggtcg gtagtagcca gcacgcatag   360
caccagctgg agggtcccga tgatctcgat gcccaggccc tggcccgagt tcacaccatc   420
agccagctgc ctagacccag gccccactct gcctagaagc tggagaggcc tggggtgagc   480
tggggccttt gcatccagct gcatccaggc cagggtattc tggggtacca agaccagagg   540
caaggggcga gccccaggca tgaaggtgat ggtcaggagc actcctagga aagagatgc    600
aaaaaggtgg aaggcccag cagggacac ggcttcatac ccaaaagtcc agaacat        657
```

<210> SEQ ID NO 10
<211> LENGTH: 465
<212> TYPE: DNA
<213> ORGANISM: Homo sapiens

<400> SEQUENCE: 10

```
atgcagtcgg gcatggggtg gaatgttctg gacttttggc tggctgatgg tgtgaactcg    60
ggccagggcc tgggcatcga gatcatcggg accctccagc tggtgctatg cgtgctggct   120
actaccgacc ggaggcgccg tgaccttggt ggctcagccc ccttgccat cggcctctct   180
gtagcccttg acacctcct ggctattgac tacactggct gtgggattaa ccctgctcgg   240
tcctttggct ccgcgtgat cacacacaac ttcagcaacc actggatttt ctgggtgggg   300
ccattcatcg ggggagccct ggctgtactc atctacgact tcatcctggc cccacgcagc   360
agtgacctca cagaccgcgt gaaggtgtgg accagcggcc aggtggagga gtatgacctg   420
gatgccgacg acatcaactc cagggtggag atgaagccca aatag                   465
```

<210> SEQ ID NO 11
<211> LENGTH: 154
<212> TYPE: PRT
<213> ORGANISM: Homo sapiens

<400> SEQUENCE: 11

Met Gln Ser Gly Met Gly Trp Asn Val Leu Asp Phe Trp Leu Ala Asp
1               5                   10                  15

Gly Val Asn Ser Gly Gln Gly Leu Gly Ile Glu Ile Ile Gly Thr Leu
                20                  25                  30

Gln Leu Val Leu Cys Val Leu Ala Thr Thr Asp Arg Arg Arg Arg Asp
            35                  40                  45

Leu Gly Gly Ser Ala Pro Leu Ala Ile Gly Leu Ser Val Ala Leu Gly
        50                  55                  60

His Leu Leu Ala Ile Asp Tyr Thr Gly Cys Gly Ile Asn Pro Ala Arg
65                  70                  75                  80

Ser Phe Gly Ser Ala Val Ile Thr His Asn Phe Ser Asn His Trp Ile
                85                  90                  95

Phe Trp Val Gly Pro Phe Ile Gly Gly Ala Leu Ala Val Leu Ile Tyr
                100                 105                 110

Asp Phe Ile Leu Ala Pro Arg Ser Ser Asp Leu Thr Asp Arg Val Lys
            115                 120                 125

Val Trp Thr Ser Gly Gln Val Glu Glu Tyr Asp Leu Asp Ala Asp Asp
        130                 135                 140

Ile Asn Ser Arg Val Glu Met Lys Pro Lys
145                 150

<210> SEQ ID NO 12
<211> LENGTH: 465
<212> TYPE: DNA
<213> ORGANISM: Homo sapiens

<400> SEQUENCE: 12
ctatttgggc ttcatctcca ccctggagtt gatgtcgtcg gcatccaggt catactcctc        60
cacctggccg ctggtccaca ccttcacgcg gtctgtgagg tcactgctgc gtggggccag       120
gatgaagtcg tagatgagta cagccagggc tcccccgatg aatggcccca cccagaaaat       180
ccagtggttg ctgaagttgt gtgtgatcac cgcggagcca aggaccgagc agggttaat        240 cccacagcca gtgtagtcaa tagccaggag gtgtccaagg ctacagaga ggccgatggc        300 aaggggggct gagccaccaa ggtcacggcg cctccggtcg gtagtagcca gcacgcatag       360
caccagctgg agggtcccga tgatctcgat gcccaggccc tggcccgagt tcacaccatc       420
agccagccaa aagtccagaa cattccaccc catgcccgac tgcat                       465

<210> SEQ ID NO 13
<211> LENGTH: 810
<212> TYPE: DNA
<213> ORGANISM: Mus musculus

<400> SEQUENCE: 13
atggccagtg aaatcaagaa gaagctcttc tggagggctg tggtggctga gttcctggcc        60
atgaccctct tcgtcttcat cagcattggt tctgccctag cttcaattac cccactggag       120
agaaaccaga cgctggtcca ggacaacgtg aaggtgtcgc tggccttttgg tttgagcatc      180 gctactctgg cccaaagtgt gggtcacatc agcggtgctc acctcaaccc tgcggtcaca       240
ctggggctcc tgctcagctg tcagatcagc atcctccggg ctgtcatgta catcatcgcc       300
cagtgtgtgg gagccatcgt cgccacggcc attctctcgg gcatcacctc ctccctagtc       360
gacaattcac ttggccgcaa tgacctggct cacggtgtga actctggcca gggcctgggc       420

| | |
|---|---:|
| attgagatca ttggcactct gcagctggta ctgtgcgttc tggccaccac tgaccggagg | 480 |
| cgccgagact taggtggctc agccccgctt gccattggct tgtctgtggc ccttggacac | 540 |
| ctgctggcga ttgactacac tggctgcggt atcaaccctg cccggtcatt tggctctgct | 600 |
| gtgctcaccc gcaacttctc aaaccactgg attttctggg tggggccgtt cattgggggt | 660 |
| gccctggcag tgctcatcta tgacttcatc ctggccccac gcagcagcga cttcacagac | 720 |
| cgcatgaagg tgtggaccag tggccaggtg gaggagtatg acctggatgc tgacgacatc | 780 |
| aactccaggg tggagatgaa gcccaaatag | 810 |

```
<210> SEQ ID NO 14
<211> LENGTH: 269
<212> TYPE: PRT
<213> ORGANISM: Mus musculus

<400> SEQUENCE: 14
```

Met Ala Ser Glu Ile Lys Lys Lys Leu Phe Trp Arg Ala Val Val Ala
1               5                   10                  15

Glu Phe Leu Ala Met Thr Leu Phe Val Phe Ile Ser Ile Gly Ser Ala
            20                  25                  30

Leu Gly Phe Asn Tyr Pro Leu Glu Arg Asn Gln Thr Leu Val Gln Asp
        35                  40                  45

Asn Val Lys Val Ser Leu Ala Phe Gly Leu Ser Ile Ala Thr Leu Ala
    50                  55                  60

Gln Ser Val Gly His Ile Ser Gly Ala His Leu Asn Pro Ala Val Thr
65                  70                  75                  80

Leu Gly Leu Leu Leu Ser Cys Gln Ile Ser Ile Leu Arg Ala Val Met
                85                  90                  95

Tyr Ile Ile Ala Gln Cys Val Gly Ala Ile Val Ala Thr Ala Ile Leu
            100                 105                 110

Ser Gly Ile Thr Ser Ser Leu Val Asp Asn Ser Leu Gly Arg Asn Asp
        115                 120                 125

Leu Ala His Gly Val Asn Ser Gly Gln Gly Leu Gly Ile Glu Ile Ile
    130                 135                 140

Gly Thr Leu Gln Leu Val Leu Cys Val Leu Ala Thr Thr Asp Arg Arg
145                 150                 155                 160

Arg Arg Asp Leu Gly Gly Ser Ala Pro Leu Ala Ile Gly Leu Ser Val
                165                 170                 175

Ala Leu Gly His Leu Leu Ala Ile Asp Tyr Thr Gly Cys Gly Ile Asn
            180                 185                 190

Pro Ala Arg Ser Phe Gly Ser Ala Val Leu Thr Arg Asn Phe Ser Asn
        195                 200                 205

His Trp Ile Phe Trp Val Gly Pro Phe Ile Gly Gly Ala Leu Ala Val
    210                 215                 220

Leu Ile Tyr Asp Phe Ile Leu Ala Pro Arg Ser Ser Asp Phe Thr Asp
225                 230                 235                 240

Arg Met Lys Val Trp Thr Ser Gly Gln Val Glu Glu Tyr Asp Leu Asp
                245                 250                 255

Ala Asp Asp Ile Asn Ser Arg Val Glu Met Lys Pro Lys
            260                 265

```
<210> SEQ ID NO 15
<211> LENGTH: 810
<212> TYPE: DNA
<213> ORGANISM: Mus musculus
```

<400> SEQUENCE: 15

```
ctatttgggc ttcatctcca ccctggagtt gatgtcgtca gcatccaggt catactcctc    60
cacctggcca ctggtccaca ccttcatgcg gtctgtgaag tcgctgctgc gtggggccag   120
gatgaagtca tagatgagca ctgccagggc acccccaatg aacggcccca cccagaaaat   180
ccagtggttt gagaagttgc gggtgagcac agcagagcca aatgaccggg cagggttgat   240
accgcagcca gtgtagtcaa tcgccagcag gtgtccaagg ccacagaca agccaatggc    300
aagcggggct gagccaccta agtctcggcg cctccggtca gtggtggcca gaacgcacag   360
taccagctgc agagtgccaa tgatctcaat gcccaggccc tggccagagt tcacaccgtg   420
agccaggtca ttgcggccaa gtgaattgtc gactaggag gaggtgatgc ccgagagaat    480
ggccgtggcg acgatggctc ccacacactg ggcgatgatg tacatgacag cccggaggat   540
gctgatctga cagctgagca ggagccccag tgtgaccgca gggttgaggt gagcaccgct   600
gatgtgaccc acactttggg ccagagtagc gatgctcaaa ccaaaggcca gcgacacctt   660
cacgttgtcc tggaccagcg tctggttctct ctccagtggg taattgaagc ctagggcaga   720
accaatgctg atgaagacga agagggtcat ggccaggaac tcagccacca cagccctcca   780
gaagagcttc ttcttgattt cactggccat                                    810
```

<210> SEQ ID NO 16
<211> LENGTH: 4123
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (312)..(312)
<223> OTHER INFORMATION: n is a, c, g, or t

<400> SEQUENCE: 16

```
gcggccgcga tctatacatt gaatcaatat tggcaattag ccatattagt cattggttat    60
atagcataaa tcaatattgg ctattggcca ttgcatacgt tgtatctata tcataatatg   120
tacatttata ttggctcatg tccaatatga ccgccatgtt gacattgatt attgactagt   180
tattaatagt aatcaattac ggggtcatta gttcatagcc catatatgga gttccgcgtt   240
acataactta cggtaaatgg cccgcctggc tgaccgccca acgaccccg cccattgacg    300
tcaataatga cntatgttcc catagtaacg ccaatagga ctttccattg acgtcaatgg    360
gtggagtatt tacggtaaac tgcccacttg gcagtacatc aagtgtatca tatgccaagt   420
ccgcccccta ttgacgtcaa tgacggtaaa tggcccgcct ggcattatgc ccagtacatg   480
accttacggg actttcctac ttggcagtac atctacgtat tagtcatcgc tattaccatg   540
gtgatgcggt tttggcagta caccaatggg cgtggatagc ggtttgactc acggggattt   600
ccaagtctcc accccattga cgtcaatggg agtttgtttt ggcaccaaaa tcaacgggac   660
tttccaaaat gtcgtaataa ccccgccccg ttgacgcaaa tgggcggtag gcgtgtacgg   720
tgggaggtct atataagcag agctcgttta gtgaaccgtc agatccggtc gcgcgaattc   780
gagctcggta ccagctctca gagggaattg agcaccggc agcggtctca ggccaagccc    840
cctgccagca tggccagcga gttcaagaag aagctcttct ggagggcagt ggtggccgag   900
ttcctggcca cgaccctctt tgtcttcatc agcatcggtt ctgccctggg cttcaaatac   960
ccggtgggga acaaccagac ggcggtccag gacaacgtga aggtgtcgct ggccttcggg  1020
ctgagcatcg ccacgctggc gcagagtgtg ggccacatca gcggcgccca cctcaacccg  1080
```

```
gctgtcacac tggggctgct gctcagctgc cagatcagca tcttccgtgc cctcatgtac    1140
atcatcgccc agtgcgtggg ggccatcgtc gccaccgcca tcctctcagg catcacctcc    1200
tccctgactg ggaactcgct tggccgcaat gacctggctg atggtgtgaa ctcgggccag    1260
ggcctgggca tcgagatcat cgggaccctc cagctggtgc tatgcgtgct ggctactacc    1320
gaccggaggc gccgtgacct tggtggctca gccccccttg ccatcggcct ctctgtagcc    1380
cttggacacc tcctggctat tgactacact ggctgtggga ttaaccctgc tcggtccttt    1440
ggctccgcgg tgatcacaca caacttcagc aaccactgga ttttctgggt ggggccattc    1500 atcggggag ccctggctgt actcatctac gacttcatcc tggccccacg cagcagtgac     1560
ctcacagacc gcgtgaaggt gtggaccagc ggccaggtgg aggagtatga cctggatgcc    1620
gacgacatca actccagggt ggagatgaag cccaaataga aggggtctgg cccgggcatc    1680
cacgtagggg gcaggggcag gggcgggcgg agggagggga ggggtgaaat ccatactgta    1740
gacactctga caagctggcc aaagtcactt ccccaagatc tgccagacct gcatggtcaa    1800
gcctcttatg ggggtgtttc tatctctttc tttctctttc tgtttcctgg cctcagagct    1860
tcctggggac caagatttac caattcaccc actcccttga agttgtggag gaggtgaaag    1920
aaagggaccc acctgctagt cgcccctcag agcatgatgg gaggtgtgcc agaaagtccc    1980
ccctcgcccc aaagttgctc accgactcac ctgcgcaagt gcctgggatt ctaccgtaat    2040
tgctttgtgc ctttgggcac ggccctcctt cttttcctaa catgcacctt gctcccaatg    2100
gtgcttggag gggaagaga tcccaggagg tgcagtggag gggcaagct ttgctccttc      2160 agttctgctt gctcccaagc ccctgacccg ctcggactta ctgcctgacc ttggaatcgt    2220
ccctatatca gggcctgagt gacctccttc tgcaaagtgg cagggaccgg cagagctcta    2280
caggcctgca gcccctaagt gcaaacacag catgggtcca aagacgtgg tctagaccag     2340 ggctgctctt tccacttgcc ctgtgttctt tccccagggg catgactgtc gccacacgcc    2400
tctgtgtaca tgtgtgcaga gcagacaggc tacaaagcag agatcgacag acagccaggt    2460
agttggaact ttctgttccc tatggagagg cttccctaca cagggcctgc tattgcagaa    2520
tgaagccatt tagagggtga aggagaaata cccatgttac ttctctgagt tttagttggt    2580
ctttccatct atcactgcat tatcttgctc attcttcagt tctctactcc ctcttgtcag    2640
tgtagacaca ggtcaccatt atgctggtgt atgtttatca aagagcactt gagctgtctg    2700
aagcccaaag cctgaggaca gaaagaccct gatgcaggtc agcccatgga ggcagatgcc    2760
cttgctgggc ctgggggttt tccaagcctt cagctggtcc tgaccaggat ggagcaagct    2820
cttcccttgc tcatgagctc ctgatcagag gcatttgagc agctgaataa cctgcacagg    2880
cttgctgtat gaccctggc cacagccttc cctctgcatt gacctggagg ggagaggtca     2940
gccttgacct aatgaggtag ctatagttgc agcccaagga cagttcagag atcaggatca    3000
gctttgaagg ctggattcta tctacataag tcctttcaat tccaccaggg ccagagcagc    3060
tccaccactg tgcacttagc catgatggca acagaaacca agagacacaa ttacgcaggt    3120
atttagaagc agagggacaa ccagaaggcc cttaactatc accagtgcat cacatctgca    3180
cactctcttc tccattccct agcaggaact tctagctcat ttaacagata aagaaactga    3240
ggcccacggt ttcagctaga caatgatttg gccaggccta gtaaccaagg ccctgtctct    3300
ggctactccc tggaccacga ggctgattcc tctcatttcc agcttctcag tttctgcctg    3360
ggcaatggcc aggggccagg agtggggaga gttgtgatgg aggggagagg ggtcacaccc    3420
```

| | |
|---|---|
| acccccctgcc tggttctagg ctgctgcaca ccaaggccct gcatctgtct gctctgcata | 3480 |
| tatgtctctt tggagttgga atttcattat atgttaagaa aataaaggaa aatgacttgt | 3540 |
| aaggtcaaaa aaaaaaaacc ggaattcgat atcaagctta tcgataccgt cgacctcgag | 3600 |
| ggggggcccg cgcttggcgt aatcatggtc atagctgttc cggatcctct agagtcgacc | 3660 |
| tgcaggcatg caagcttggg atctttgtga aggaacctta cttctgtggt gtgacataat | 3720 |
| tggacaaact acctacagag atttaaagct ctaaggtaaa tataaaattt ttaagtgtat | 3780 |
| aatgtgttaa actactgatt ctaattgttt gtgtatttta gattcacagt cccaaggctc | 3840 |
| atttcaggcc cctcagtcct cacagtctgt tcatgatcat aatcagccat accacatttg | 3900 |
| tagaggtttt acttgcttta aaaaacctcc cacacctccc cctgaacctg aaacataaaa | 3960 |
| tgaatgcaat tgttgttgtt aacttgttta ttgcagctta taatggttac aaataaagca | 4020 |
| atagcatcac aaatttcaca aataaagcat tttttcact gcattctagt tgtggtttgt | 4080 |
| ccaaactcat caatgtatct tatcatgtct ggatcgcggc cgc | 4123 |

<210> SEQ ID NO 17
<211> LENGTH: 4123
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3812)..(3812)
<223> OTHER INFORMATION: n is a, c, g, or t

<400> SEQUENCE: 17

| | |
|---|---|
| gcggccgcga tccagacatg ataagataca ttgatgagtt tggacaaacc acaactagaa | 60 |
| tgcagtgaaa aaaatgcttt atttgtgaaa tttgtgatgc tattgcttta tttgtaacca | 120 |
| ttataagctg caataaacaa gttaacaaca caattgcat tcattttatg tttcaggttc | 180 |
| aggggggaggt gtgggaggtt ttttaaagca agtaaaacct ctacaaatgt ggtatggctg | 240 |
| attatgatca tgaacagact gtgaggactg aggggcctga atgagccctt gggactgtga | 300 |
| atctaaaata cacaaacaat tagaatcagt agtttaacac attatacact taaaaatttt | 360 |
| atatttacct tagagcttta aatctctgta ggtagtttgt ccaattatgt cacaccacag | 420 |
| aagtaaggtt ccttcacaaa gatcccaagc ttgcatgcct gcaggtcgac tctagaggat | 480 |
| ccggaacagc tatgaccatg attacgccaa gcgcgggccc cccctcgagg tcgacggtat | 540 |
| cgataagctt gatatcgaat tccggttttt tttttttgac cttacaagtc atttcctttt | 600 |
| atttctttaa catataatga aattccaact ccaaagagac atatatgcag agcagacaga | 660 |
| tgcagggcct tggtgtgcag cagcctagaa ccaggcaggg ggtgggtgtg accccctctcc | 720 |
| cctccatcac aactctcccc actcctggcc cctggccatt gcccaggcag aaactgagaa | 780 |
| gctggaaatg agaggaatca gcctcgtggt ccagggagta gccagagaca gggccttggt | 840 |
| tactaggcct ggccaaatca ttgtctagct gaaaccgtgg gcctcagttt ctttatctgt | 900 |
| taaatgagct agaagttcct gctagggaat ggagaagaga gtgtgcagat gtgatgcact | 960 |
| ggtgatagtt aagggccttc tggttgtccc tctgcttcta aatacctgcg taattgtgtc | 1020 |
| tcttggtttc tgttgccatc atggctaagt gcacagtggt ggagctgctc tggccctggt | 1080 |
| ggaattgaaa ggactttatgt agatagaatc cagccttcaa agctgatcct gatctctgaa | 1140 |
| ctgtccttgg gctgcaacta tagctacctc attaggtcaa gctgacctc tcccctccag | 1200 |
| gtcaatgcag agggaaggct gtggccaggg gtcatacagc aagcctgtgc aggttattca | 1260 |

```
gctgctcaaa tgcctctgat caggagctca tgagcaaggg aagagcttgc tccatcctgg    1320
tcaggaccag ctgagggctt ggaaaacccc caggcccagc aagggcatct gcctccatgg    1380
gctgacctgc atcagggtct ttctgtcctc aggctttggg cttcagacag ctcaagtgct    1440 cttttgataaa catacaccag cataatggtg acctgtgtct acactgacaa gagggagtag    1500
agaactgaag aatgagcaag ataatgcagt gatagatgga aagaccaact aaaactcaga    1560
gaagtaacat gggtatttct ccttcaccct ctaaatggct tcattctgca atagcaggcc    1620
ctgtgtaggg aagcctctcc atagggaaca gaaagttcca actacctggc tgtctgtcga    1680
tctctgcttt gtagcctgtc tgctctgcac acatgtacac agaggcgtgt ggcgacagtc    1740
atgcccctgg ggaaagaaca cagggcaagt ggaaagagca gccctggtct agaccacgtc    1800
ttctggaccc atgctgtgtt tgcacttagg ggctgcaggc ctgtagagct ctgccggtcc    1860
ctgccacttt gcagaaggag gtcactcagg ccctgatata gggacgattc caaggtcagg    1920
cagtaagtcc gagcgggtca ggggcttggg agcaagcaga actgaaggag caaagcttgc    1980
cccctccact gcacctcctg ggatctcttc cccctccaag caccattggg agcaaggtgc    2040
atgttaggaa agaaggagg gccgtgccca aggcacaaa gcaattacgg tagaatccca    2100
ggcacttgcg caggtgagtc ggtgagcaac tttggggcga gggggggactt tctggcacac    2160 ctcccatcat gctctgaggg gcgactagca ggtgggtccc tttctttcac ctcctccaca    2220
acttcaaggg agtgggtgaa ttggtaaatc ttggtcccca ggaagctctg aggccaggaa    2280
acagaaagag aaagaaagag atagaaacac ccccataaga ggcttgacca tgcaggtctg    2340
gcagatcttg gggaagtgac tttggccagc ttgtcagagt gtctacagta tggatttcac    2400
ccctcccctc cctccgcccg cccctgcccc tgcccctac gtggatgccc gggcagacc    2460 ccttctatt gggcttcatc tccaccctgg agttgatgtc gtcggcatcc aggtcatact    2520
cctccacctg gccgctggtc cacaccttca cgcggtctgt gaggtcactg ctgcgtgggg    2580
ccaggatgaa gtcgtagatg agtacagcca gggctccccc gatgaatggc cccacccaga    2640
aaatccagtg gttgctgaag ttgtgtgtga tcaccgcgga gccaaaggac cgagcagggt    2700
taatcccaca gccagtgtag tcaatagcca ggaggtgtcc aagggctaca gagaggccga    2760
tggcaagggg ggctgagcca ccaaggtcac ggcgcctccg gtcggtagta gccagcacgc    2820
atagcaccag ctggagggtc ccgatgatct cgatgcccag gccctggccc gagttcacac    2880
catcagccag gtcattgcgg ccaagcgagt tcccagtcag ggaggaggtg atgcctgaga    2940
ggatggcggt ggcgacgatg gcccccacgc actgggcgat gatgtacatg agggcacgga    3000
agatgctgat ctggcagctg agcagcagcc ccagtgtgac agccgggttg aggtgggcgc    3060
cgctgatgtg gcccacactc tgcgccacgcg tggcgatgct cagcccgaag ccagcgaca    3120 ccttcacgtt gtcctggacc gccgtctggt tgttccccac cgggtatttg aagcccaggg    3180
cagaaccgat gctgatgaag acaaagaggg tcgtggccag gaactcggcc accactgccc    3240
tccagaagag cttcttcttg aactcgctgg ccatgctggc agggggcttg gcctgagacc    3300
gctgccgggt gctcaattcc ctctgagagc tggtaccgag ctcgaattcg cgcgaccgga    3360
tctgacggtt cactaaacga gctctgctta tatagacctc ccaccgtaca cgcctaccgc    3420
ccatttgcgt caacggggcg gggttattac gacatttttgg aaagtcccgt tgatttttggt    3480 gccaaaacaa actcccattg acgtcaatgg ggtggagact tggaaatccc cgtgagtcaa    3540
accgctatcc acgccattg gtgtactgcc aaaaccgcat caccatggta atagcgatga    3600
```

| ctaatacgta gatgtactgc caagtaggaa agtcccgtaa ggtcatgtac tgggcataat | 3660 |
| gccaggcggg ccatttaccg tcattgacgt caatagggggg cggacttggc atatgataca | 3720 |
| cttgatgtac tgccaagtgg gcagtttacc gtaaatactc cacccattga cgtcaatgga | 3780 |
| aagtccctat tggcgttact atgggaacat angtcattat tgacgtcaat gggcgggggt | 3840 |
| cgttgggcgg tcagccaggc gggccattta ccgtaagtta tgtaacgcgg aactccatat | 3900 |
| atgggctatg aactaatgac cccgtaattg attactatta ataactagtc aataatcaat | 3960 |
| gtcaacatgg cggtcatatt ggacatgagc caatataaat gtacatatta tgatatagat | 4020 |
| acaacgtatg caatggccaa tagccaatat tgatttatgc tatataacca atgactaata | 4080 |
| tggctaattg ccaatattga ttcaatgtat agatcgcggc cgc | 4123 |

<210> SEQ ID NO 18
<211> LENGTH: 8605
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (939)..(939)
<223> OTHER INFORMATION: n is a, c, g, or t

<400> SEQUENCE: 18

| cttcagcatc ttttactttc accagcgttt ctgggtgagc aaaaacagga aggcaaaatg | 60 |
| ccgcaaaaaa gggaataagg gcgacacgga aatgttgaat actcatactc ttcctttttc | 120 |
| aatatattg aagcatttat cagggttatt gtgtcatgag cggatacata tttgaatgta | 180 |
| tttagaaaaa taaacaaata ggggttccgc gcacatttcc ccgaaaagtg ccacctgacg | 240 |
| tctaagaaac cattattatc atgacattaa cctataaaaa taggcgtatc acgaggccct | 300 |
| ttcgtcttca agaattcgcg cgaccggatc cgggcaacgt tgttgccatt gctgcaggcg | 360 |
| gagaactggt aggtatggaa gatctttggc cactccctct ctgcgcgctc gctcgctcac | 420 |
| tgaggccggg cgaccaaagg tcgcccgacg cccgggcttt gcccgggcgg cctcagtgag | 480 |
| cgagcgagcg cgcagagagg gagtggccaa ctccatcact aggggttcct ggaggggtgg | 540 |
| agtcgtgacg tgaattacgt catagggtta gggaggtcct gtattagagg tcacgagctc | 600 |
| ggtaccgtcg acgcggccgc acgcgtcacg gccgcgatct atacattgaa tcaatattgg | 660 |
| caattagcca tattagtcat tggttatata gcataaatca atattggcta ttggccattg | 720 |
| catacgttgt atctatatca taatatgtac atttatattg gctcatgtcc aatatgaccg | 780 |
| ccatgttgac attgattatt gactagttat taatagtaat caattacggg gtcattagtt | 840 |
| catagcccat atatggagtt ccgcgttaca taacttacgg taaatggccc gcctggctga | 900 |
| ccgcccaacg acccccgccc attgacgtca ataatgacnt atgttcccat agtaacgcca | 960 |
| atagggactt tccattgacg tcaatgggtg gagtatttac ggtaaactgc ccacttggca | 1020 |
| gtacatcaag tgtatcatat gccaagtccg cccctattg acgtcaatga cggtaaatgg | 1080 |
| cccgcctggc attatgccca gtacatgacc ttacgggact ttcctacttg gcagtacatc | 1140 |
| tacgtattag tcatcgctat taccatggtg atgcggtttt ggcagtacac caatgggcgt | 1200 |
| ggatagcggt ttgactcacg gggatttcca agtctccacc ccattgacgt caatgggagt | 1260 |
| ttgttttggc accaaaatca acgggacttt ccaaaatgtc gtaataaccc cgccccgttg | 1320 |
| acgcaaatgg gcggtaggcg tgtacggtgg gaggtctata taagcagagc tcgtttagtg | 1380 |
| aaccgtcaga tccggtcgcg cgaattcgag ctcggtacca gctctcagag ggaattgagc | 1440 |

```
acccggcagc ggtctcaggc caagcccct gccagcatgg ccagcgagtt caagaagaag      1500
ctcttctgga gggcagtggt ggccgagttc ctggccacga ccctctttgt cttcatcagc      1560
atcggttctg ccctgggctt caaatacccg gtggggaaca accagacggc ggtccaggac      1620
aacgtgaagg tgtcgctggc cttcgggctg agcatcgcca cgctggcgca gagtgtgggc      1680
cacatcagcg gcgcccacct caacccggct gtcacactgg ggctgctgct cagctgccag      1740
atcagcatct tccgtgccct catgtacatc atcgcccagt gcgtggggc catcgtcgcc      1800 accgccatcc tctcaggcat cacctcctcc ctgactggga actcgcttgg ccgcaatgac      1860
ctggctgatg tgtgaactc gggccagggc ctgggcatcg agatcatcgg gaccctccag      1920
ctggtgctat gcgtgctggc tactaccgac cggaggcgcc gtgaccttgg tggctcagcc      1980 cccccttgcca tcggcctctc tgtagccctt ggacacctcc tggctattga ctacactggc      2040
tgtgggatta accctgctcg gtcctttggc tccgcggtga tcacacacaa cttcagcaac      2100
cactggattt tctgggtggg gccattcatc ggggagccc tggctgtact catctacgac      2160
ttcatcctgg ccccacgcag cagtgacctc acagaccgcg tgaaggtgtg gaccagcggc      2220
caggtggagg agtatgacct ggatgccgac gacatcaact ccagggtgga gatgaagccc      2280
aaatagaagg ggtctggccc gggcatccac gtaggggca ggggcagggg cgggcggagg      2340
gagggagggg gtgaaatcca tactgtagac actctgacaa gctggccaaa gtcacttccc      2400
caagatctgc cagacctgca tggtcaagcc tcttatgggg gtgtttctat ctctttcttt      2460
ctctttctgt ttcctggcct cagagcttcc tggggaccaa gatttaccaa ttcacccact      2520
cccttgaagt tgtggaggag gtgaaagaaa gggacccacc tgctagtcgc ccctcagagc      2580
atgatgggag gtgtgccaga aagtccccc tcgcccaaa gttgctcacc gactcacctg      2640
cgcaagtgcc tgggattcta ccgtaattgc tttgtgcctt gggcacggc cctccttctt      2700 ttcctaacat gcaccttgct cccaatggtg cttggagggg gaagagatcc caggaggtgc      2760
agtggagggg gcaagctttg ctccttcagt tctgcttgct cccaagcccc tgacccgctc      2820
ggacttactg cctgaccttg gaatcgtccc tatatcaggg cctgagtgac ctccttctgc      2880
aaagtggcag ggaccggcag agctctacag gcctgcagcc cctaagtgca aacacagcat      2940
gggtccagaa gacgtggtct agaccagggc tgctcttcc acttgccctg tgttctttcc      3000
ccaggggcat gactgtcgcc acacgcctct gtgtacatgt gtgcagagca gacaggctac      3060
aaagcagaga tcgacagaca gccaggtagt tggaactttc tgttccctat ggagaggctt      3120
ccctacacag ggcctgctat tgcagaatga agccatttag agggtgaagg agaaatacccc      3180 atgttacttc tctgagtttt agttggtctt tccatctatc actgcattat cttgctcatt      3240
cttcagttct ctactccctc ttgtcagtgt agacacaggt caccattatg ctggtgtatg      3300
tttatcaaag agcacttgag ctgtctgaag cccaaagcct gaggacagaa agaccctgat      3360
gcaggtcagc ccatggaggc agatgccctt gctgggcctg ggggttttcc aagccctcag      3420
ctggtcctga ccaggatgga gcaagctctt cccttgctca tgagctcctg atcagaggca      3480
tttgagcagc tgaataacct gcacaggctt gctgtatgac ccctggccac agccttccct      3540
ctgcattgac ctggagggga gaggtcagcc ttgacctaat gaggtagcta tagttgcagc      3600
ccaaggacag ttcagagatc aggatcagct ttgaaggctg gattctatct acataagtcc      3660
tttcaattcc accagggcca gagcagctcc accactgtgc acttagccat gatggcaaca      3720
gaaaccaaga gacacaatta cgcaggtatt tagaagcaga gggacaacca gaaggccctt      3780
```

```
aactatcacc agtgcatcac atctgcacac tctcttctcc attccctagc aggaacttct    3840
agctcattta acagataaag aaactgaggc ccacggtttc agctagacaa tgatttggcc    3900
aggcctagta accaaggccc tgtctctggc tactccctgg accacgaggc tgattcctct    3960
catttccagc ttctcagttt ctgcctgggc aatggccagg ggccaggagt ggggagagtt    4020
gtgatggagg ggagagggt cacacccacc ccctgcctgg ttctaggctg ctgcacacca    4080
aggccctgca tctgtctgct ctgcatatat gtctctttgg agttggaatt tcattatatg    4140
ttaagaaaat aaaggaaaat gacttgtaag gtcaaaaaaa aaaaccgga attcgatatc    4200
aagcttatcg ataccgtcga cctcgagggg gggcccgcgc ttggcgtaat catggtcata    4260
gctgttccgg atcctctaga gtcgacctgc aggcatgcaa gcttgggatc tttgtgaagg    4320
aaccttactt ctgtggtgtg ataattgg acaaactacc tacagagatt taaagctcta    4380
aggtaaatat aaaatttta agtgtataat gtgttaaact actgattcta attgtttgtg    4440
tattttagat tcacagtccc aaggctcatt tcaggcccct cagtcctcac agtctgttca    4500
tgatcataat cagccatacc acatttgtag aggtttact tgctttaaaa aacctcccac    4560
acctcccct gaacctgaaa cataaaatga atgcaattgt tgttgttaac ttgtttattg    4620
cagcttataa tggttacaaa taagcaata gcatcacaaa tttcacaaat aaagcatttt    4680
tttcactgca ttctagttgt ggtttgtcca aactcatcaa tgtatcttat catgtctgga    4740
tcgcggccgt agataagtag catggcgggt taatcattaa ctacaaggaa ccctagtga    4800
tggagttggc cactccctct ctgcgcgctc gctcgctcac tgaggccggg cgaccaaagg    4860
tcgcccgacg cccgggcttt gcccgggcgg cctcagtgag cgagcgagcg cgcagagagg    4920
gagtggccaa agatctctag agctctacgc cggacgcatc gtggccggca tcaccggcgc    4980
cacaggtgcg gttgctggcg cctatatcgc cgacatcacc gatggggaag atcgggctcg    5040
ccacttcggg ctcatgagcg cttgtttcgg cgtgggtatg gtggcaggcc ccgtggccgg    5100
gggactgttg ggcgccatct ccttgcatgc accattcctt gcggcggcgg tgctcaacgg    5160
cctcaaccta ctactgggct gcttcctaat gcaggagtcg cataagggag agcgtcgacc    5220
gatgcccttg agagccttca acccagtcag ctccttccgg tgggcgcggg gcatgactat    5280
cgtcgccgca cttatgactg tcttctttat catgcaactc gtaggacagg tgccggcagc    5340
gctctgggtc attttcggcg aggaccgctt tcgctggagc gcgacgatga tcggcctgtc    5400
gcttgcggta ttcggaatct tgcacgccct cgctcaagcc ttcgtcactg gtcccgccac    5460
caaacgtttc ggcgagaagc aggccattat cgccggcatg gcggccgacg cgctgggcta    5520
cgtcttgctg gcgttcgcga cgcgaggctg gatggccttc cccattatga ttcttctcgc    5580
ttccggcggc atcgggatgc ccgcgttgca ggccatgctg tccaggcagg tagatgacga    5640
ccatcaggga cagcttcaag gatcgctcgc ggctcttacc agcctaactt cgatcactgg    5700
accgctgatc gtcacggcga tttatgccgc ctcggcgagc acatggaacg ggttggcatg    5760
gattgtaggc gccgccctat accttgtctg cctccccgcg ttgcgtcgcg gtgcatggag    5820
ccgggccacc tcgacctgaa tggaagccgg cggcacctcg ctaacggatt caccactcca    5880
agaattggag ccaatcaatt cttgcggaga actgtgaatg cgcaaaccaa cccttggcag    5940
aacatatcca tcgcgtccgc catctccagc agccgcacgc ggcgcatctc gggcagcgtt    6000
gggtcctggc cacgggtgcg catgatcgtg ctcctgtcgt tgaggacccg gctaggctgg    6060
cggggttgcc ttactggtta gcagaatgaa tcaccgatac gcgagcgaac gtgaagcgac    6120
tgctgctgca aaacgtctgc gacctgagca acaacatgaa tggtcttcgg tttccgtgtt    6180
```

```
tcgtaaagtc tggaaacgcg gaagtcagcg ccctgcacca ttatgttccg gatctgcatc    6240
gcaggatgct gctggctacc ctgtggaaca cctacatctg tattaacgaa gcgctggcat    6300
tgaccctgag tgattttcct ctggtcccgc cgcatccata ccgccagttg tttaccctca    6360
caacgttcca gtaaccgggc atgttcatca tcagtaaccc gtatcgtgag catcctctct    6420
cgtttcatcg gtatcattac ccccatgaac agaaattccc ccttacacgg aggcatcaag    6480
tgaccaaaca ggaaaaaacc gcccttaaca tggcccgctt tatcagaagc cagacattaa    6540
cgcttctgga gaaactcaac gagctggacg cggatgaaca ggcagacatc tgtgaatcgc    6600
ttcacgacca cgctgatgag ctttaccgca gctgcctcgc gcgtttcggt gatgacggtg    6660
aaaacctctg acacatgcag ctcccggaga cggtcacagc ttgtctgtaa gcggatgccg    6720
ggagcagaca gcccgtcag ggcgcgtcag cgggtgttgg cgggtgtcgg ggcgcagcca    6780
tgacccagtc acgtagcgat agcggagtgt atactggctt aactatgcgg catcagagca    6840
gattgtactg agagtgcacc atatgcggtg tgaaataccg cacagatgcg taaggagaaa    6900
ataccgcatc aggcgctctt ccgcttcctc gctcactgac tcgctgcgct cggtcgttcg    6960
gctgcggcga gcggtatcag ctcactcaaa ggcggtaata cggttatcca cagaatcagg    7020
ggataacgca ggaaagaaca tgtgagcaaa aggccagcaa aaggccagga accgtaaaaa    7080
ggccgcgttg ctggcgtttt tccataggct ccgcccccct gacgagcatc acaaaaatcg    7140
acgctcaagt cagaggtggc gaaacccgac aggactataa agataccagg cgtttccccc    7200
tggaagctcc ctcgtgcgct ctcctgttcc gaccctgccg cttaccggat acctgtccgc    7260
ctttctccct tcgggaagcg tggcgctttc tcaatgctca cgctgtaggt atctcagttc    7320
ggtgtaggtc gttcgctcca agctgggctg tgtgcacgaa ccccccgttc agcccgaccg    7380
ctgcgcctta tccggtaact atcgtcttga gtccaacccg gtaagacacg acttatcgcc    7440
actgggagga gccactggta acaggattag cagagcgagg tatgtaggcg gtgctacaga    7500
gttcttgaag tggtggccta actacggcta cactagaagg acagtatttg gtatctgcgc    7560
tctgctgaag ccagttacct tcggaaaaag agttggtagc tcttgatccg gcaaacaaac    7620
caccgctggt agcggtggtt ttttgtttg caagcagcag attacgcgca gaaaaaaagg    7680
atctcaagaa gatcctttga tcttttctac ggggtctgac gctcagtgga acgaaaactc    7740
acgttaaggg attttggtca tgagattatc aaaaaggatc ttcacctaga tccttttaaa    7800
ttaaaaatga agttttaaat caatctaaag tatatatgag taaacttggt ctgacagtta    7860
ccaatgctta atcagtgagg cacctatctc agcgatctgt ctatttcgtt catccatagt    7920
tgcctgactc cccgtcgtgt agataactac gatacgggag ggcttaccat ctggccccag    7980
tgctgcaatg ataccgcgag acccacggct ccagatttat cagcaataaa ccagccagcc    8040
ggaagggccg agcgcagaag tggtcctgca actttatccg cctccatcca gtctattaat    8100
tgttgccggg aagctagagt aagtagttcg ccagttaata gtttgcgcaa cgttgttgcc    8160
attgctgcag gcatcgtggt gtcacgctcg tcgtttggta tggcttcatt cagctccggt    8220
tcccaacgat caaggcgagt tacatgatcc cccatgttgt gcaaaaaagc ggttagctcc    8280
ttcggtcctc cgatcgttgt cagaagtaag ttggccgcag tgttatcact catggttatg    8340
gcagcactgc ataattctct tactgtcatg ccatccgtaa gatgcttttc tgtgactggt    8400
gagtactcaa ccaagtcatt ctgagaatag tgtatgcggc gaccgagttg ctcttgcccg    8460
gcgtcaacac gggataatac cgcgccacat agcagaactt taaaagtgct catcattgga    8520
```

```
aaacgttctt cggggcgaaa actctcaagg atcttaccgc tgttgagatc cagttcgatg    8580
taacccactc gtgcacccaa ctgat                                           8605

<210> SEQ ID NO 19
<211> LENGTH: 8605
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7667)..(7667)
<223> OTHER INFORMATION: n is a, c, g, or t

<400> SEQUENCE: 19
atcagttggg tgcacgagtg ggttacatcg aactggatct caacagcggt aagatccttg      60
agagttttcg ccccgaagaa cgttttccaa tgatgagcac ttttaaagtt ctgctatgtg     120
gcgcggtatt atcccgtgtt gacgccgggc aagagcaact cggtcgccgc atacactatt     180
ctcagaatga cttggttgag tactcaccag tcacagaaaa gcatcttacg gatggcatga     240
cagtaagaga attatgcagt gctgccataa ccatgagtga taacactgcg gccaacttac     300
ttctgacaac gatcggagga ccgaaggagc taaccgcttt tttgcacaac atggggatc      360 atgtaactcg ccttgatcgt tgggaaccgg agctgaatga agccatacca aacgacgagc     420
gtgacaccac gatgcctgca gcaatggcaa caacgttgcg caaactatta actggcgaac     480
tacttactct agcttcccgg caacaattaa tagactggat ggaggcggat aaagttgcag     540
gaccacttct gcgctcggcc cttccggctg gctggtttat tgctgataaa tctggagccg     600
tgggtctcgc ggtatcattg cagcactggg gccagatggt aagccctccc gtatcgtagt     660
tatctacacg acggggagtc aggcaactat ggatgaacga atagacaga tcgctgagat      720 aggtgcctca ctgattaagc attggtaact gtcagaccaa gtttactcat atatacttta     780
gattgattta aaacttcatt tttaatttaa aaggatctag gtgaagatcc ttttttgataa     840 tctcatgacc aaaatccctt aacgtgagtt tcgttccac tgagcgtcag accccgtaga      900
aaagatcaaa ggatcttctt gagatccttt ttttctgcgc gtaatctgct gcttgcaaac     960
aaaaaaacca ccgctaccag cggtggtttg tttgccggat caagagctac caactctttt    1020
tccgaaggta actggcttca gcagagcgca gataccaaat actgtccttc tagtgtagcc    1080
gtagttaggc caccacttca agaactctgt agcaccgcct acatacctcg ctctgctaat    1140
cctgttacca gtggctcctc ccagtggcga taagtcgtgt cttaccgggt tggactcaag    1200
acgatagtta ccggataagg cgcagcggtc gggctgaacg gggggttcgt gcacacagcc    1260
cagcttggag cgaacgacct acaccgaact gagataccta cagcgtgagc attgagaaag    1320
cgccacgctt cccgaaggga gaaaggcgga caggtatccg gtaagcggca gggtcggaac    1380
aggagagcgc acgagggagc ttccagggg aaacgcctgg tatctttata gtcctgtcgg     1440
gtttcgccac ctctgacttg agcgtcgatt tttgtgatgc tcgtcagggg ggcggagcct    1500
atggaaaaac gccagcaacg cggccttttt acggttcctg gccttttgct ggccttttgc    1560
tcacatgttc tttcctgcgt tatccctga ttctgtggat aaccgtatta ccgcctttga     1620
gtgagctgat accgctcgcc gcagccgaac gaccgagcgc agcgagtcag tgagcgagga    1680
agcggaagag cgcctgatgc ggtattttct ccttacgcat ctgtgcggta tttcacaccg    1740
catatggtgc actctcagta caatctgctc tgatgccgca tagttaagcc agtatacact    1800
ccgctatcgc tacgtgactg ggtcatggct gcgccccgac acccgccaac acccgctgac    1860
```

```
gcgccctgac gggcttgtct gctcccggca tccgcttaca gacaagctgt gaccgtctcc      1920
gggagctgca tgtgtcagag gttttcaccg tcatcaccga aacgcgcgag gcagctgcgg      1980
taaagctcat cagcgtggtc gtgaagcgat tcacagatgt ctgcctgttc atccgcgtcc      2040
agctcgttga gtttctccag aagcgttaat gtctggcttc tgataaagcg gccatgtta      2100 agggcggttt tttcctgttt ggtcacttga tgcctccgtg taaggggaa tttctgttca      2160 tgggggtaat gataccgatg aaacgagaga ggatgctcac gatacgggtt actgatgatg      2220
aacatgcccg gttactggaa cgttgtgagg gtaaacaact ggcggtatgg atgcggcggg      2280
accagagaaa aatcactcag ggtcaatgcc agcgcttcgt taatacagat gtaggtgttc      2340
cacagggtag ccagcagcat cctgcgatgc agatccggaa cataatggtg cagggcgctg      2400
acttccgcgt ttccagactt tacgaaacac ggaaaccgaa gaccattcat gttgttgctc      2460
aggtcgcaga cgttttgcag cagcagtcgc ttcacgttcg ctcgcgtatc ggtgattcat      2520
tctgctaacc agtaaggcaa ccccgccagc ctagccgggt cctcaacgac aggagcacga      2580
tcatgcgcac ccgtggccag gacccaacgc tgcccgagat gcgccgcgtg cggctgctgg      2640
agatggcgga cgcgatggat atgttctgcc aagggttggt ttgcgcattc acagttctcc      2700
gcaagaattg attggctcca attcttggag tggtgaatcc gttagcgagg tgccgccggc      2760
ttccattcag gtcgaggtgg cccggctcca tgcaccgcga cgcaacgcgg ggaggcagac      2820
aaggtatagg gcggcgccta caatccatgc caacccgttc catgtgctcg ccgaggcggc      2880
ataaatcgcc gtgacgatca gcggtccagt gatcgaagtt aggctggtaa gagccgcgag      2940
cgatccttga agctgtccct gatggtcgtc atctacctgc ctggacagca tggcctgcaa      3000
cgcgggcatc ccgatgccgc cggaagcgag aagaatcata tgggggaagg ccatccagcc      3060
tcgcgtcgcg aacgccagca agacgtagcc cagcgcgtcg gccgccatgc cggcgataat      3120
ggcctgcttc tcgccgaaac gtttggtggc gggaccagtg acgaaggctt gagcgagggc      3180
gtgcaagatt ccgaataccg caagcgacag gccgatcatc gtcgcgctcc agcgaaagcg      3240
gtcctcgccg aaaatgaccc agagcgctgc cggcacctgt cctacgagtt gcatgataaa      3300
gaagacagtc ataagtgcgg cgacgatagt catgccccgc gcccaccgga aggagctgac      3360
tgggttgaag gctctcaagg gcatcggtcg acgctctccc ttatgcgact cctgcattag      3420
gaagcagccc agtagtaggt tgaggccgtt gagcaccgcc gccgcaagga atggtgcatg      3480
caaggagatg gcgcccaaca gtccccggc cacgggcct gccaccatac ccacgccgaa      3540
acaagcgctc atgagcccga agtggcgagc ccgatcttcc ccatcggtga tgtcggcgat      3600
ataggcgcca gcaaccgcac ctgtggcgcc ggtgatgccg ccacgatgc gtccggcgta      3660 gagctctaga gatctttggc cactccctct ctgcgcgctc gctcgctcac tgaggccgcc      3720
cgggcaaagc ccgggcgtcg ggcgaccttt ggtcgcccgg cctcagtgag cgagcgagcg      3780
cgcagagagg gagtggccaa ctccatcact aggggttcct tgtagttaat gattaacccg      3840
ccatgctact tatctacggc cgcgatccag acatgataag atacattgat gagtttggac      3900
aaaccacaac tagaatgcag tgaaaaaaat gctttatttg tgaaatttgt gatgctattg      3960
ctttatttgt aaccattata gctgcaata acaagttaa caacaacaat tgcattcatt      4020
ttatgtttca ggttcagggg gaggtgtggg aggttttta aagcaagtaa aacctctaca      4080
aatgtggtat ggctgattat gatcatgaac agactgtgag gactgagggg cctgaaatga      4140
gccttgggac tgtgaatcta aaatacacaa acaattagaa tcagtagttt aacacattat      4200
```

```
acacttaaaa attttatatt taccttagag ctttaaatct ctgtaggtag tttgtccaat    4260
tatgtcacac cacagaagta aggttccttc acaaagatcc caagcttgca tgcctgcagg    4320
tcgactctag aggatccgga acagctatga ccatgattac gccaagcgcg gccccccct    4380 cgaggtcgac ggtatcgata agcttgatat cgaattccgg tttttttttt ttgaccttac    4440
aagtcatttt cctttatttt cttaacatat aatgaaattc caactccaaa gagacatata    4500
tgcagagcag acagatgcag ggccttggtg tgcagcagcc tagaaccagg caggggtgg    4560 gtgtgacccc tctcccctcc atcacaactc tccccactcc tggcccctgg ccattgccca    4620
ggcagaaact gagaagctgg aaatgagagg aatcagcctc gtggtccagg gagtagccag    4680
agacagggcc ttggttacta ggcctggcca aatcattgtc tagctgaaac cgtgggcctc    4740
agtttcttta tctgttaaat gagctagaag ttcctgctag gaatggaga agagagtgtg    4800 cagatgtgat gcactggtga tagttaaggg ccttctggtt gtccctctgc ttctaaatac    4860
ctgcgtaatt gtgtctcttg gtttctgttg ccatcatggc taagtgcaca gtggtggagc    4920
tgctctggcc ctggtggaat tgaaaggact tatgtagata gaatccagcc ttcaaagctg    4980
atcctgatct ctgaactgtc cttgggctgc aactatagct acctcattag gtcaaggctg    5040
acctctcccc tccaggtcaa tgcagaggga aggctgtggc caggggtcat acagcaagcc    5100
tgtgcaggtt attcagctgc tcaaatgcct ctgatcagga gctcatgagc aagggaagag    5160
cttgctccat cctggtcagg accagctgag ggcttggaaa accccaggc ccagcaaggg    5220 catctgcctc catgggctga cctgcatcag ggtctttctg tcctcaggct ttgggcttca    5280
gacagctcaa gtgctctttg ataaacatac accagcataa tggtgacctg tgtctacact    5340
gacaagaggg agtagagaac tgaagaatga gcaagataat gcagtgatag atggaaagac    5400
caactaaaac tcagagaagt aacatgggta tttctccttc accctctaaa tggcttcatt    5460
ctgcaatagc aggccctgtg tagggaagcc tctccatagg gaacagaaag ttccaactac    5520
ctggctgtct gtcgatctct gctttgtagc ctgtctgctc tgcacacatg tacacagagg    5580
cgtgtggcga cagtcatgcc cctggggaaa gaacacaggg caagtggaaa gagcagccct    5640
ggtctagacc acgtcttctg gacccatgct gtgtttgcac ttaggggctg caggcctgta    5700
gagctctgcc ggtccctgcc actttgcaga aggaggtcac tcaggccctg atatagggac    5760
gattccaagg tcaggcagta agtccgagcg ggtcaggggc ttgggagcaa gcagaactga    5820
aggagcaaag cttgcccct ccactgcacc tcctgggatc tcttcccct ccaagcacca    5880 ttgggagcaa ggtgcatgtt aggaaaagaa ggagggccgt gcccaaggc acaaagcaat    5940 tacggtagaa tcccaggcac ttgcgcaggt gagtcggtga gcaactttgg ggcgaggggg    6000
gactttctgg cacacctccc atcatgtctct gagggcgac tagcaggtgg gtccctttct    6060
ttcacctcct ccacaacttc aagggagtgg gtgaattggt aaatcttggt ccccaggaag    6120
ctctgaggcc aggaaacaga aagagaaaga aagagataga aacaccccca taagaggctt    6180
gaccatgcag gtctggcaga tcttggggaa gtgactttgg ccagcttgtc agagtgtcta    6240
cagtatggat ttcaccccctc ccctccctcc gcccgcccct gcccctgccc cctacgtgga    6300
tgcccgggcc agacccttc tatttgggct tcatctccac cctggagttg atgtcgtcgg    6360
catccaggtc atactcctcc acctggccgc tggtccacac cttcacgcgg tctgtgaggt    6420
cactgctgcg tggggccagg atgaagtcgt agatgagtac agccagggct ccccgatga    6480 atggccccac ccagaaaatc cagtggttgc tgaagttgtg tgtgatcacc gcggagccaa    6540
aggaccgagc agggttaatc ccacagccag tgtagtcaat agccaggagg tgtccaaggg    6600
```

```
ctacagagag gccgatggca aggggggctg agccaccaag gtcacggcgc ctccggtcgg    6660
tagtagccag cacgcatagc accagctgga gggtcccgat gatctcgatg cccaggccct    6720
ggcccgagtt cacaccatca gccaggtcat tgcggccaag cgagttccca gtcagggagg    6780
aggtgatgcc tgagaggatg gcggtggcga cgatggcccc cacgcactgg gcgatgatgt    6840
acatgagggc acggaagatg ctgatctggc agctgagcag cagccccagt gtgacagccg    6900
ggttgaggtg ggcgccgctg atgtggccca cactctgcgc cagcgtggcg atgctcagcc    6960
cgaaggccag cgacaccttc acgttgtcct ggaccgccgt ctggttgttc cccaccgggt    7020
atttgaagcc cagggcagaa ccgatgctga tgaagacaaa gagggtcgtg gccaggaact    7080
cggccaccac tgccctccag aagagcttct tcttgaactc gctggccatg ctggcagggg    7140
gcttggcctg agaccgctgc cgggtgctca attccctctg agagctggta ccgagctcga    7200
attcgcgcga ccggatctga cggttcacta aacgagctct gcttatatag acctcccacc    7260
gtacacgcct accgcccatt tgcgtcaacg gggcggggtt attacgacat tttggaaagt    7320
cccgttgatt ttggtgccaa aacaaactcc cattgacgtc aatgggtgg  agacttggaa    7380 atccccgtga gtcaaaccgc tatccacgcc cattggtgta ctgccaaaac cgcatcacca    7440
tggtaatagc gatgactaat acgtagatgt actgccaagt aggaaagtcc cgtaaggtca    7500
tgtactgggc ataatgccag gcgggccatt taccgtcatt gacgtcaata ggggcggac    7560 ttggcatatg atacacttga tgtactgcca agtgggcagt ttaccgtaaa tactccaccc    7620
attgacgtca atggaaagtc cctattggcg ttactatggg aacatangtc attattgacg    7680
tcaatgggcg ggggtcgttg ggcggtcagc caggcgggcc atttaccgta agttatgtaa    7740
cgcggaactc catatatggg ctatgaacta atgaccccgt aattgattac tattaataac    7800
tagtcaataa tcaatgtcaa catggcggtc atattggaca tgagccaata taaatgtaca    7860
tattatgata tagatacaac gtatgcaatg gccaatagcc aatattgatt tatgctatat    7920
aaccaatgac taatatggct aattgccaat attgattcaa tgtatagatc gcggccgtga    7980
cgcgtgcggc cgcgtcgacg gtaccgagct cgtgacctct aatacaggac ctccctaacc    8040
ctatgacgta attcacgtca cgactccacc cctccaggaa ccccctagtga tggagttggc    8100 cactccctct ctgcgcgctc gctcgctcac tgaggccgcc cgggcaaagc ccgggcgtcg    8160
ggcgaccttt ggtcgcccgg cctcagtgag cgagcgagcg cgcagagagg gagtggccaa    8220
agatcttcca tacctaccag ttctccgcct gcagcaatgg caacaacgtt gcccggatcc    8280
ggtcgcgcga attcttgaag acgaaagggc ctcgtgatac gcctattttt ataggttaat    8340
gtcatgataa taatggtttc ttagacgtca ggtggcactt ttcggggaaa tgtgcgcgga    8400
acccctattt gtttattttt ctaaatacat tcaaatatgt atccgctcat gacacaataa    8460
ccctgataaa tgcttcaata atattgaaaa aggaagagta tgagtattca acatttccgt    8520
gtcgccctta ttcccttttt tgcggcattt tgccttcctg tttttgctca cccagaaacg    8580
ctggtgaaag taaaagatgc tgaag                                          8605
```

AAV MEDIATED AQUAPORIN GENE TRANSFER TO TREAT SJOGREN'S SYNDROME

CROSS REFERENCE TO RELATED APPLICATIONS

This application is a national stage application under 35 U.S.C. 371 and claims the benefit of International Application No. PCT/US2013/057632, having an international filing date of Aug. 30, 2013, which designated the United States, which PCT application claims the benefit of U.S. Provisional Patent Application Serial No. 61/695,753 entitled "AAV MEDIATED AQUAPORIN-1 GENE TRANSFER TO TREAT SJOGREN'S SYNDROME" filed Aug. 31, 2012, the contents of each of which is are incorporated herein in their entirety by reference.

REFERENCE TO SEQUENCE LISTING

This application contains a Sequence Listing submitted as an electronic text file named "6137NIDCR-14-PUS_sequence_listing_ST25.txt", having a size in bytes of 53 KB, and created on Aug. 30, 2013. The information contained in this electronic file is hereby incorporated by reference in its entirety pursuant to 37 CFR § 1.52(e)(5).

FIELD

The present invention relates to the use of gene therapy to protect individuals suffering from Sjögren's syndrome, from Sjögren's syndrome-related xerostomia. It also relates to treating Sjögren's syndrome-related xerostomia in individuals suffering from such xerostomia. More specifically, the present invention relates to adeno-associated virus vectors and virions that encode aquaporin-1 protein, and the use of such vectors and virions to treat a subject suffering from Sjögren's syndrome-related xerostomia.

BACKGROUND/INTRODUCTION

Sjögren's syndrome is a systemic autoimmune disease in which immune cells attack and destroy the exocrine glands that produce saliva and tears. Sjögren's syndrome can also affect multiple organs, including kidneys and lungs. It is estimated that approximately 4 million people in the United States suffer from Sjögren's syndrome. Nine out of ten Sjögren's patients are women, with the average age of onset being in the late 40s. Sjögren's syndrome can occur in all age groups of both women and men. Sjögren's syndrome can occur independently, referred to as primary Sjögren's syndrome, or may develop years after the onset of an associated rheumatic disorder, referred to as secondary Sjögren's syndrome. The prevalence of primary Sjögren's syndrome varies from about 0.05% to 5% of the population, and the incidence of diagnosed cases has been reported to be about 4 per 100,000 people yearly (Kok et al., 2003, *Ann Rhem Dis* 62, 11038-1046).

Xerostomia (dry mouth) and xerophthalmia (conjunctivitis sicca, dry eyes) are hallmarks of Sjögren's syndrome (Fox et al., 1985, *Lancet* 1, 1432-1435) Immunologically-activated or apoptotic glandular epithelial cells that expose autoantigens in predisposed individuals might drive auto-immune-mediated tissue injury (see, e.g., Voulgarelis et al, 2010m Nat Rev Rheumatol 6, 529-537; Xanthou et al, 1999, *Clin Exp Immunol* 118, 154-163) Immune activation is typically presented as focal, mononuclear (T, B and macrophage) cell infiltrates proximal to the ductal epithelial cells (epithelitis) and forms sialadenitis (see, e.g., Voulgarelis et al., ibid.). Though the pathogenetic mechanism for this autoimmune exocrinopathy has not been fully elucidated, it has been shown that CD4+T-lymphocytes constitute 60-70 percent of the mononuclear cells infiltrating the glands (see, e.g., Skopouli et al., 1991, *J Rheumatol* 18, 210-214). Abnormal activation of proinflammatory Th1 (see, e.g., Bombardierei et al., 2004, *Arthritis Res Ther* 6, R447-R456; Vosters et al., 2009, *Arthritis Rheum* 60, 3633-3641) and Th17 (see, e.g., Nguyen et al., 2008, *Arthritis and Rheumatism* 58, 734-743) cells have been reported to be central to induction of SS in either human or animal models.

Activation of Th1 and Th17 cells is initiated by antigen presentation, which requires the engagement not only of the T-cell receptor (TCR) to MHC molecules from antigen presenting cells (APCs), but also appropriate costimulatory signaling (see, e.g., Smith-Garvin et al., 2009, *Ann Rev Immunol* 27, 591-619). One of the crucial pathways of costimulation is the interaction of CD28 on the T cell with B7.1 (CD80)/B7.2 (CD86) on antigen presenting cells. Cytotoxic T-lymphocyte antigen 4 (CTLA-4; also referred to as CD152) displays a wide range of activities in immune tolerance. The main function of CTLA-4 is to bind to B7 and compete for its interaction with CD28, thereby shutting down the B7:CD28 pathway and subsequently initiating the deactivation of the T cell response and maintaining immune homostasis (see, e.g., Perkins et al., 1996, *J Immunol* 156, 4154-4159). Moreover, CTLA-4 is constitutively expressed on CD4+CD25+Foxp3+ natural regulatory T cells (nTreg), which play a crucial role in immune tolerance and ultimately protection from autoimmune disease (see, e.g., Sakaguchi et al., 2006, *Immunological Reviews* 212, 8-27). CTLA-4 is required by nTreg cells for suppressing the immune responses by affecting the potency of APCs to activate effective T cells (see, e.g., Wing et al., 2008, *Science* 322, 271-275; Takahashi et al., 2000, *J Exp Med* 192, 303-310). It is known that T cell autoimmunity is controlled by the balances between Th17/Treg cells (see, e.g., Eisenstein et al., 2009, *Pediatric* Research 65, 26R-31R) and Th1/Th2 cells (see, e.g., Nicholson et al., 1996, *Current Opinion Immunol* 8, 837-842). Thus, CTLA-4 could represent an important therapeutic target, shifting the T cell balance from proinflammatory T17 and/or Th1 towards suppressing Treg and/or Th2 cells. Other immunological manifestations of Sjögren's syndrome include the formation of auto-reactive antibodies such as anti-nuclear antibodies (ANA), SSA antibodies (e.g., SSA/Ro), SSB antibodies (e.g., SSB/La), and M3R antibodies.

While some treatments that have proven effective for certain autoimmune diseases, such as rheumatoid arthritis, currently there are no effective therapies for the treatment of Sjögren's syndrome. For example, anti-tumor necrosis factor (TNF) agents have been shown to have beneficial effects in the treatment of rheumatoid arthritis as well as in other inflammatory arthritides and diseases. Etanercept (ENBREL™), a fusion protein of soluble TNF receptor 2 and the Fc region of immunoglobulin IgG1, is marketed for a number of such conditions. However, Etanercept has been shown to be ineffective in a clinical trial of patients with Sjögren's syndrome (see, e.g., Moutsopoulos et al., 2008, *Ann Rheum Dis* 67, 1437-1443). In addition, administration of an AAV vector encoding soluble TNF receptor 1-Fc fusion protein to the salivary glands of a murine model of Sjögren's syndrome has been shown to have a negative effect on salivary gland function (see, e.g., Vosters et al., 2009, *Arthritis Res Ther* 11, R189).

As discussed above, one hallmark of Sjögren's syndrome is xerostomia (dry mouth), resulting from immune system-mediated destruction of the salivary glands and the consequent loss of the ability to produce saliva. Aquaporin-1 (AQP-1; formerly known as CHIP28) is a 28-kilodalton protein present in renal tubules and erythrocytes, which has similarity to other membrane channels proteins (see, e.g., Preston and Agre, 1991, *PNAS* 88, pp 11110-11114). AQP-1 is plasma membrane protein that forms channels in the membrane, thus facilitating rapid transmembrane water movement in response to an osmotic gradient. Although members of this family generally show only about 30% identity, several features are preserved. For example, the overall size of each subunit is approximately 30 kDa. Furthermore, hydropathy analyses of these proteins are similar, suggesting six transmembrane helices and having two Asn-Pro-Ala signature motifs (or close variants). A detailed structural analysis of AQP-1 has been described by Heymann et al., *Journal of Structural Biology* 121, 191-206 (1998), which is incorporated by reference, herein in its entirety. Similarly, a family of aquaporin proteins have been identified, including AQP-2, AQP-3, AQP-4, AQP-5, AQP-6, AQP-7, AQP-8, AQP-9, AQP-10, and AQP-11, Previous work has attempted to use virus-mediated transfer of a gene encoding AQP-1 to restore fluid secretion in the parotid glands of miniature pigs that had been irradiated to destroy parotid gland function (see, e.g., Gao et al., 2011, *Gene Therapy*, 18, pp 38-42). However, there are no reports of anyone trying to restore salivary flow in patients suffering from Sjögren's syndrome as the cause of the xerostomia in this disease is thought to be immune related such as auto antibodies or proinflammatory cytokines.

Thus, there remains a need for an effective composition to protect subjects from, and treat subjects for, xerostomia associated with Sjögren's syndrome.

SUMMARY

The disclosure provides a gene transfer-based method to protect a subject from Sjögren's syndrome-related xerostomia. The method comprises administering to the subject an AAV vector, or a virion comprising such a vector, that encodes an aquaporin (AQP) protein. Also provided are methods to produce such AQP proteins, AAV vectors, and AAV virions. Also provided are nucleic acid molecules that encode AQP proteins of the invention and uses thereof.

The disclosure provides a treatment for Sjögren's syndrome-related xerostomia. Such a treatment comprises an AAV vector, or a virion comprising such a vector, that encodes an AQP-1 protein. Administration of such a treatment to a subject protects the subject from Sjögren's syndrome-related xerostomia.

The disclosure also provides a preventative for Sjögren's syndrome-related xerostomia. Such a preventative comprises an AAV vector, or a virion comprising such a vector, that encodes an AQP-1 protein. Administration of such a preventative to a subject protects the subject from Sjögren's syndrome-related xerostomia.

The invention provides a salivary gland cell transfected with an AAV vector that encodes an AQP-1 protein. The salivary gland cell can be that of a subject with Sjögren's syndrome.

The disclosure also provides an AAV virion comprising an AAV vector that encodes an AQP-1 protein for the treatment or prevention of Sjögren's syndrome-related xerostomia. Also provided is the use of an AAV vector, or a virion comprising such a vector that encodes an AQP-1 protein for the manufacture of a medicament to protect a subject from Sjögren's syndrome-related xerostomia.

DETAILED DESCRIPTION

Figure 1:
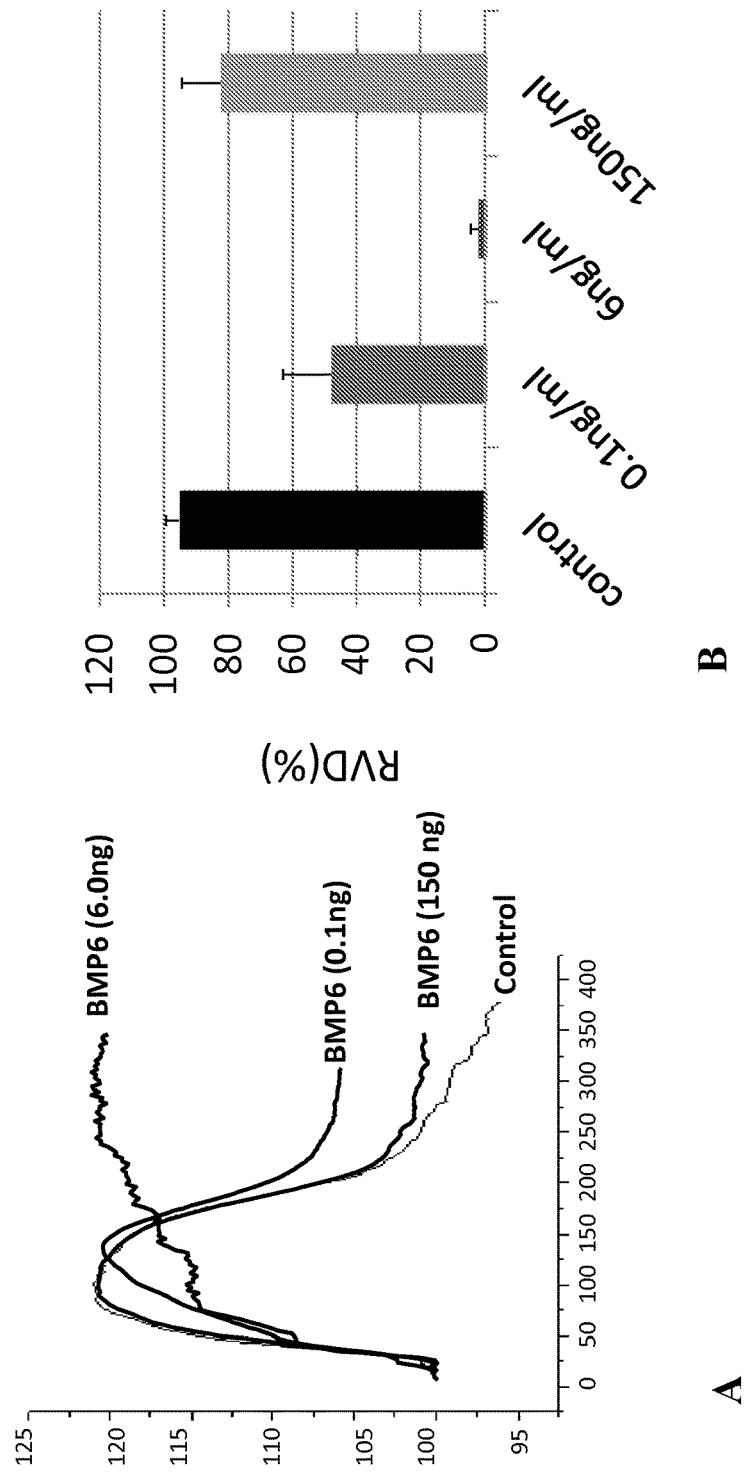
FIG. 1. In vitro measurement of RVD after treatment with BMP-6 on HSG cells. A) BMP6 induces volume change of HSG cells, the cells were place in the HTS solution in the presence of different dosages of BMP-6 (1 ng, 6 ng or 150 ng), or/and without BMP-6 as control. B) Dosage response curve of BMP-6 induces cell volume change. The 6 ng shows significant inhibition of recovery of cell volume change, data are presented as mean±S.E.

It will be understood that this invention is not limited to particular invention described, as such may, of course, vary. It is also to be understood that the terminology used herein is for the purpose of describing particular invention only, and is not intended to be limiting, since the scope of the present invention will be limited only by the claims.

As used herein and in the appended claims, the singular forms "a," "an," and "the" include plural referents unless the context clearly dictates otherwise. It is further noted that the claims may be drafted to exclude any optional element. For example, a nucleic acid molecule refers to one or more nucleic acid molecules. As such, the terms "a", "an", "one or more" and "at least one" can be used interchangeably. This statement is intended to serve as antecedent basis for use of such exclusive terminology as "solely," "only" and the like in connection with the recitation of claim elements, or use of a "negative" limitation. Similarly the terms "comprising", "including" and "having" can be used interchangeably.

As used herein, the terms isolated, isolating, purified, and the like, do not necessarily refer to the degree of purity of a cell or molecule of the present invention. Such terms instead refer to cells or molecules that have been separated from their natural milieu or from components of the environment in which they are produced. For example, a naturally occurring cell or molecule (e.g., a DNA molecule, a protein, etc.) present in a living animal, including humans, is not isolated. However, the same cell, or molecule, separated from some or all of the coexisting materials in the animal, is considered isolated. As a further example, according to the present invention, protein molecules that are present in a sample of blood obtained from an individual would be considered isolated. It should be appreciated that protein molecules obtained from such a blood sample using further purification steps would also be referred to as isolated, in accordance with the notion that isolated does not refer to the degree of purity of the protein.

It is understood by those skilled in the art that the sequence of a protein can vary, or be altered, with little or no affect on the activity of that protein. According to the present invention, such proteins are referred to as variants, allelic variants, mutants, isoforms, or homologues. Such variants can arise naturally as a result of an individual carrying two different alleles that encode allelic variants, or they can be constructed using techniques such as genetic engineering. With regard to the nomenclature of proteins and their variants, one form of the protein may arbitrarily be designated as the reference form (e.g., wild-type) and other forms designated as mutants, variants, isoforms or homologues. For example, if a particular allele, and thus its encoded protein, is associated with a particular phenotypic characteristic (e.g., the absence of a disease), or is found in the majority of a population, the encoded form of the protein may be referred to as a "wild-type form", while other forms may be referred to as variants, mutants, isoforms, or homologues. With regard to the present invention, a protein comprising the sequence of SEQ ID NO:2, SEQ ID NO:5, SEQ ID NO:8, SEQ ID NO:11 or SEQ ID NO:14 will be considered the wild-type (wt) protein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and materials for which the publications are cited.

It is to be appreciated that certain features of the invention, which are, for clarity, described in the context of separate invention, may also be provided in combination in a single embodiment. Conversely, various features of the invention, which are, for brevity, described in the context of a single embodiment, may also be provided separately or in any suitable sub-combination. All combinations of the invention are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

The present invention provides a novel gene therapy to protect a subject from Sjögren's syndrome-related xerostomia. The inventors have discovered that administration of an adeno-associated virus (AAV) virion comprising an AAV vector that encodes an aquaporin-1 (AQP-1) protein to a subject protects that subject from Sjögren's syndrome-related xerostomia. This discovery is surprising because the mechanism of Sjögren's syndrome is thought to be autoimmune. For example, Sjögren's syndrome is characterized by chronic inflammation in the secretory epithelia, and the loss of gland function is thought to be related to this ongoing inflammation. One mechanism proposed for this loss of gland function in Sjögren's syndrome is the production of autoantibodies that bind muscarinic receptors on the surface of acinar cells, thereby blocking signals that trigger acinar cell function. Given such a mechanism, it is surprising that salivary function can be restored by introduction of AQP-1 since it would be expected that continuing antibody production would inhibit acinar cell function.

Proteins

As used herein, an aquaporin protein, also referred to as AQP protein, is any protein that exhibits activity of an exemplary aquaporin protein (e.g., human aquaporin), such the ability to form a channel that allows the passage of water.

An AQP protein can have a wild-type (wt) AQP sequence (i.e., it has the same amino acid sequence as a natural AQP protein), can be any portion of a wt AQP protein, or it can be a variant of the natural AQP protein, provided that such a portion or variant retains the ability to form a channel that allows the passage of water. Assays to determine the ability of an AQP protein of the present invention to form a channel that allows the passage of water are known to those skilled in the art (see, for example, Lui et al., Journal of Biological Chemistry 281, 15485-15495 (2006)).

In one embodiment, a protein useful in the methods of the present invention is an AQP-1 protein comprising the entire amino acid sequence of a naturally occurring AQP-1 protein. One example of an AQP-1 protein is NCBI Reference No. NP_932766.1 (SEQ ID NO:2). Another example of an AQP-1 protein is NCBI Reference No. NP_001171989.1 (SEQ ID NO:5). Another example of an AQP-1 protein is NCBI Reference No (SEQ ID NO:8). Another example of an AQP-1 protein is NCBI Reference No. NP_001171990.1 (SEQ ID NO:11). Another example of an AQP-1 protein is NCBI Reference No. NP_001171991.1 (SEQ ID NO:14).

In another embodiment, a protein useful in the methods of the present invention is an AQP protein comprising the amino acid sequence of a naturally occurring AQP protein selected from AQP-2, AQP-3, AQP-4, AQP-5, AQP-6, AQP-7, AQP-8, AQP-9, AQP-10, and AQP-11. Examples of these AQP proteins are known in the art, such as NCBI Reference No. NP 000477 (AQP-2), NCBI Reference No. NP_004916 (AQP-3), NCBI Reference No. NP_001641 (AQP-4), NCBI Reference No. NP_001642 (AQP-5), NCBI Reference No. NP_001643 (AQP-6), NCBI Reference No. NP_001161 (AQP-7), NCBI Reference No. NP_066190 (AQP-9).

In one embodiment, an AQP-1 protein is a portion of the amino acid sequence of an AQP-1 protein, wherein such portion of an AQP-1 protein retains the ability to form a channel in a cell membrane that allows the passage of water. It is also known in the art that several isoforms of AQP-1 protein exist. Thus, in one embodiment, an AQP-1 protein is an isoform of an AQP-1 protein, wherein such isoform retains the ability to form a channel that allows the passage of water. In one embodiment, an AQP-1 protein is a portion of an isoform or other naturally-occurring variant of an AQP-1 protein, wherein such portion retains the ability to form a channel in a membrane that allows the passage of water. Methods to produce functional portions and variants of AQP-1 proteins, such as conservative variants, of AQP-1 protein are known to those skilled in the art.

Also encompassed in the present invention are AQP-1 protein variants that have been altered by genetic manipulation. With regard to such variants, any type of alteration in the amino acid sequence is permissible so long as the variant retains at least one AQP-1 protein activity described herein. Examples of such variations include, but are not limited to, amino acid deletions, amino acid insertions, amino acid substitutions and combinations thereof. For example, it is well understood by those skilled in the art that one or more (e.g., 2, 3, 4, 5, 6, 7, 8, 9 or 10), amino acids can often be removed from the amino and/or carboxy terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein.

As noted, isolated variant proteins of the present invention can also contain amino acid substitutions as compared to the wild-type AQP-1 protein disclosed herein. Any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

Naturally occurring residues may be divided into classes based on side chain properties:
1) hydrophobic: Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, *J. Mol. Biol.* 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological invention, as in the present case. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. For example, amino acid substitutions can be used to identify important residues of the AQP-1 protein, or to increase or decrease the affinity of the AQP-1 proteins described herein. Exemplary amino acid substitutions are shown below in Table 1.

TABLE 1

Amino Acid Substitutions

| Original Amino Acid | Exemplary Substitutions |
| --- | --- |
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

Thus, in one embodiment of the present invention, the AQP-1 protein variant comprises at least one amino acid substitution, wherein the substitution is a conservative substitution. In one embodiment, the original amino acid is substituted with a substitution shown in Table 1.

While proteins of the present invention can consist entirely of the sequences disclosed herein, and the disclosed variants thereof, such proteins may additionally contain amino acid sequences that do not confer AQP-1 activity, but which have other useful functions. Any useful, additional amino acid sequence can be added to the isolated protein sequence, so long as the additional sequences do not have an unwanted effect on the protein's ability to form a channel that allows the passage of water. For example, isolated proteins of the present invention can contain amino acid sequences that are useful for visualizing or purifying the peptide. Such sequences act as labels (e.g., enzymes) or tags (e.g., antibody binding sites). Examples of such labels and tags include, but are not limited to, β-galacosidase, luciferase, glutathione-s-transferase, thioredoxin, HIS-tags, biotin tags, and fluorescent tags. Other useful sequences for labeling and tagging proteins are known to those of skill in the art.

In addition to the modifications described above, isolated proteins of the present invention can be further modified, so long as such modification does not significantly affect the ability of the protein to form a channel that allows the passage of water. Such modifications can be made, for example, to increase the stability, solubility or absorbability of the protein. Examples of such modifications include, but are not limited to pegylation, glycosylation, phosphorylation, acetylation, myristylation, palmitoylation, amidation and/or other chemical modification of the peptide.

An AQP-1 protein of the invention can be derived from any species that expresses a functional AQP-1 protein. An AQP-1 protein of the present invention can have the sequence of a human or other mammalian AQP-1 protein or a portion thereof. Additional examples include, but are not limited to, murine, feline, canine, equine, bovine, ovine, porcine or other companion animal, other zoo animal, or other livestock AQP-1 proteins. In one embodiment, an AQP-1 protein has the amino acid sequence of a human AQP-1 protein or portion thereof. An example of a human-derived AQP-1 amino acid sequence is a sequence selected from the group consisting of SEQ ID NO:2, SEQ ID NO:5, SEQ ID NO:8, and SEQ ID NO:11. In one embodiment, an AQP-1 protein has the amino acid sequence of a murine AQP-1 protein or a portion thereof. An example of a murine-derived AQP-1 amino acid sequence is that depicted in SEQ ID NO:14. In one embodiment, an AQP-1 protein is derived from the species that is being protected from Sjögren's syndrome-related xerostomia. In one embodiment, an AQP-1 protein is derived from a species for which the protein is not immunogenic in the subject being protected from Sjögren's syndrome-related xerostomia.

One embodiment of the present invention is an AQP-1 protein joined to a fusion segment; such a protein is referred to as an AQP-1 fusion protein. Such a protein has an AQP-1 protein domain (also referred to herein as AQP-1 domain) and a fusion segment. A fusion segment is an amino acid segment of any size that can enhance the properties of AQP-1 protein. For example, a fusion segment of the invention can increase the stability of an AQP-1 fusion protein, add flexibility or enhance or stabilize multimerization of the AQP-1 fusion protein. Examples of fusion segments include, without being limited to, an immunoglobulin fusion segment, an albumin fusion segment, and any other fusion segment that increases the biological half-life of the protein, provides flexibility to the protein, and/or enables or stabilizes multimerization. It is within the scope of the disclosure to use one or more fusion segments. Fusion segments can be joined to the amino terminus and/or carboxyl terminus of AQP-1 protein of the invention. As used herein, join refers to combine by attachment using genetic engineering techniques. In such an embodiment, a nucleic acid molecule encoding an AQP-1 protein is physically linked to a nucleic acid molecule encoding a fusion segment such that the two encoding sequences are in frame and the transcription product forms a continuous fusion protein. In one embodiment, an AQP-1 protein can be joined directly to a fusion segment, or an AQP-1 protein can be linked to the fusion segment by a linker of one or more amino acids.

One embodiment of the disclosure is an AQP-1 protein comprising an amino acid sequence selected from the group consisting of SEQ ID NO:2, SEQ ID NO:5, SEQ ID NO:8, SEQ ID NO:11 and SEQ ID NO:14. One embodiment is an AQP-1 protein comprising an amino acid sequence that is at least 60%, at least 65%, at least 70%, at least 75%, at least 80%, at least 85%, at least 90%, or at least 95% identical to an amino acid sequence selected from the group consisting of SEQ ID NO:2, SEQ ID NO:5, SEQ ID NO:8, SEQ ID NO:11 and SEQ ID NO:14. In one embodiment, an AQP-1 protein comprises an amino acid sequence that is at least 60% identical to an amino acid sequence selected from the group consisting of SEQ ID NO:2, SEQ ID NO:5, SEQ ID NO:8, SEQ ID NO:11 and SEQ ID NO:14. In one embodiment, an AQP-1 protein comprises an amino acid sequence that is at least 65% identical to an amino acid sequence selected from the group consisting of SEQ ID NO:2, SEQ ID NO:5, SEQ ID NO:8, SEQ ID NO:11 and SEQ ID NO:14. In one embodiment, an AQP-1 protein comprises an amino acid sequence that is at least 70% identical to an amino acid sequence selected from the group consisting of SEQ ID NO:2, SEQ ID NO:5, SEQ ID NO:8, SEQ ID NO:11 and SEQ ID NO:14. In one embodiment, an AQP-1 protein comprises an amino acid sequence that is at least 75% identical to an amino acid sequence selected from the group consisting of SEQ ID NO:2, SEQ ID NO:5, SEQ ID NO:8, SEQ ID NO:11 and SEQ ID NO:14. In one embodiment, an AQP-1 protein comprises an amino acid sequence that is at least 80% identical to an amino acid sequence selected from the group consisting of SEQ ID NO:2, SEQ ID NO:5, SEQ ID NO:8, SEQ ID NO:11 and SEQ ID NO:14. In one embodiment, an AQP-1 protein comprises an amino acid sequence that is at least 85% identical to an amino acid sequence selected from the group consisting of SEQ ID NO:2, SEQ ID NO:5, SEQ ID NO:8, SEQ ID NO:11 and SEQ ID NO:14. In one embodiment, an AQP-1 protein comprises an amino acid sequence that is at least 90% identical to an amino acid sequence selected from the group consisting of SEQ ID NO:2, SEQ ID NO:5, SEQ ID NO:8, SEQ ID NO:11 and SEQ ID NO:14. In one embodiment, an AQP-1 protein comprises an amino acid sequence that is at least 95% identical to an amino acid sequence selected from the group consisting of SEQ ID NO:2, SEQ ID NO:5, SEQ ID NO:8, SEQ ID NO:11 and SEQ ID NO:14. In each of these inventions, the respective an AQP-1 protein retains the ability to form a channel that allows the passage of water.

One embodiment is an AQP-1 fusion protein, wherein the AQP-1 domain of the fusion protein comprises an amino acid sequence that is at least 60%, at least 65%, at least 70%, at least 75%, at least 80%, at least 85%, at least 90%, or at least 95% identical to an amino acid sequence selected from the group consisting of SEQ ID NO:2, SEQ ID NO:5, SEQ ID NO:8, SEQ ID NO:11 and SEQ ID NO:14. One embodiment is an AQP-1 fusion protein, wherein the AQP-1 domain of the fusion protein comprises an amino acid sequence that is at least 60% identical to an amino acid sequence selected from the group consisting of SEQ ID NO:2, SEQ ID NO:5, SEQ ID NO:8, SEQ ID NO:11 and SEQ ID NO:14. One embodiment is an AQP-1 fusion protein, wherein the AQP-1 domain of the fusion protein comprises an amino acid sequence that is at least 65% identical to an amino acid sequence selected from the group consisting of SEQ ID NO:2, SEQ ID NO:5, SEQ ID NO:8, SEQ ID NO:11 and SEQ ID NO:14. One embodiment is an AQP-1 fusion protein, wherein the AQP-1 domain of the fusion protein comprises an amino acid sequence that is at least 70% identical to an amino acid sequence selected from the group consisting of SEQ ID NO:2, SEQ ID NO:5, SEQ ID NO:8, SEQ ID NO:11 and SEQ ID NO:14. One embodiment is an AQP-1 fusion protein, wherein the AQP-1 domain of the fusion protein comprises an amino acid sequence that is at least 75% identical to an amino acid sequence selected from the group consisting of SEQ ID NO:2, SEQ ID NO:5, SEQ ID NO:8, SEQ ID NO:11 and SEQ ID NO:14. One embodiment is an AQP-1 fusion protein, wherein the AQP-1 domain of the fusion protein comprises an amino acid sequence that is at least 80% identical to an amino acid sequence selected from the group consisting of SEQ ID NO:2, SEQ ID NO:5, SEQ ID NO:8, SEQ ID NO:11 and SEQ ID NO:14. One embodiment is an AQP-1 fusion protein, wherein the AQP-1 domain of the fusion protein comprises an amino acid sequence that is at least 85% identical to an amino acid sequence selected from the group consisting of SEQ ID NO:2, SEQ ID NO:5, SEQ ID NO:8, SEQ ID NO:11 and SEQ ID NO:14. One embodiment is an AQP-1 fusion protein, wherein the AQP-1 domain of the fusion protein comprises an amino acid sequence that is at least 90% identical to an amino acid sequence selected from the group consisting of SEQ ID NO:2, SEQ ID NO:5, SEQ ID NO:8, SEQ ID NO:11 and SEQ ID NO:14. One embodiment is an AQP-1 fusion protein, wherein the AQP-1 domain of the fusion protein comprises an amino acid sequence that is at least 95% identical to an amino acid sequence selected from the group consisting of SEQ ID NO:2, SEQ ID NO:5, SEQ ID NO:8, SEQ ID NO:11 and SEQ ID NO:14. One embodiment is an AQP-1 fusion protein comprising at least a portion of an AQP-1 protein having an amino acid sequence selected from the group consisting of SEQ ID NO:2, SEQ ID NO:5, SEQ ID NO:8, SEQ ID NO:11 and SEQ ID NO:14, and a fusion segment. In each of these embodiments, the respective AQP-1 protein retains the ability to form a channel that allows the passage of water.

Nucleic Acids

The disclosure provides nucleic acid molecules that encode an AQP-1 protein of the invention. One embodiment is a nucleic acid molecule that encodes an AQP-1 protein that is not a fusion protein. One embodiment is a nucleic acid molecule that encodes an AQP-1 fusion protein.

In one embodiment, a nucleic acid molecule encodes an AQP-1 protein comprising an amino acid sequence selected from the group consisting of SEQ ID NO:2, SEQ ID NO:5, SEQ ID NO:8, SEQ ID NO:11 and SEQ ID NO:14. One embodiment is a nucleic acid molecule that encodes an AQP-1 protein comprising an amino acid sequence that is at least 70%, at least 75%, at least 80%, at least 85%, at least 90%, or at least 95% identical to an amino acid sequence selected from the group consisting of SEQ ID NO:2, SEQ ID NO:5, SEQ ID NO:8, SEQ ID NO:11 and SEQ ID NO:14. In one embodiment, a nucleic acid molecule encodes an AQP-1 protein comprising an amino acid sequence that is at least 70% identical to an amino acid sequence selected from the group consisting of SEQ ID NO:2, SEQ ID NO:5, SEQ ID NO:8, SEQ ID NO:11 and SEQ ID NO:14. In one embodiment, a nucleic acid molecule encodes an AQP-1 protein comprising an amino acid sequence that is at least 75% identical to an amino acid sequence selected from the group consisting of SEQ ID NO:2, SEQ ID NO:5, SEQ ID NO:8, SEQ ID NO:11 and SEQ ID NO:14. In one embodiment, a nucleic acid molecule encodes an AQP-1 protein comprising an amino acid sequence that is at least 80% identical to an amino acid sequence selected from the group consisting of SEQ ID NO:2, SEQ ID NO:5, SEQ ID NO:8, SEQ ID NO:11 and SEQ ID NO:14. In one embodiment, a nucleic acid molecule encodes an AQP-1 protein comprising an amino acid sequence that is at least 85% identical to an amino acid sequence selected from the group consisting of SEQ ID NO:2, SEQ ID NO:5, SEQ ID NO:8, SEQ ID NO:11 and SEQ ID NO:14. In one embodiment, a nucleic acid molecule encodes an AQP-1 protein comprising an amino acid sequence that is at least 90% identical to an amino acid sequence selected from the group consisting of SEQ ID NO:2, SEQ ID NO:5, SEQ ID NO:8, SEQ ID NO:11 and SEQ ID NO:14. In one embodiment, an AQP-1 protein comprising an amino acid sequence that is at least 95% identical to an amino acid sequence selected from the group consisting of SEQ ID NO:2, SEQ ID NO:5, SEQ ID NO:8, SEQ ID NO:11 and SEQ ID NO:14. In each of these inventions, the AQP-1 protein encoded by the respective nucleic acid molecule retains the ability to form a channel that allows the passage of water.

In one embodiment, a nucleic acid molecule encodes an AQP-1 fusion protein comprising an amino acid sequence selected from the group consisting of SEQ ID NO:2, SEQ ID NO:5, SEQ ID NO:8, SEQ ID NO:11 and SEQ ID NO:14. One embodiment is a nucleic acid molecule that encodes an AQP-1 fusion protein, wherein the AQP-1 domain of the fusion protein comprises an amino acid sequence that is at least 70%, at least 75%, at least 80%, at least 85%, at least 90%, or at least 95% identical to an amino acid sequence selected from the group consisting of SEQ ID NO:2, SEQ ID NO:5, SEQ ID NO:8, SEQ ID NO:11 and SEQ ID NO:14. In each of these inventions, the AQP-1 protein encoded by the respective nucleic acid molecule retains the ability to form a channel that allows the passage of water.

In one embodiment, a nucleic acid molecule comprises a nucleic acid sequence selected from the group consisting of SEQ ID NO:1, SEQ ID NO:4, SEQ ID NO:7, SEQ ID NO:10 and SEQ ID NO:13. One embodiment is a nucleic acid molecule comprising a nucleic acid sequence that is at least 70%, at least 75%, at least 80%, at least 85%, at least 90%, or at least 95% identical to nucleic acid sequence selected from the group consisting of SEQ ID NO:1, SEQ ID NO:4, SEQ ID NO:7, SEQ ID NO:10 and SEQ ID NO:13. One embodiment is a nucleic acid molecule comprising a nucleic acid sequence that is at least 70% identical to nucleic acid sequence selected from the group consisting of SEQ ID NO:1, SEQ ID NO:4, SEQ ID NO:7, SEQ ID NO:10 and SEQ ID NO:13. One embodiment is a nucleic acid molecule comprising a nucleic acid sequence that is at least 75% identical to nucleic acid sequence selected from the group consisting of SEQ ID NO:1, SEQ ID NO:4, SEQ ID NO:7, SEQ ID NO:10 and SEQ ID NO:13. One embodiment is a nucleic acid molecule comprising a nucleic acid sequence that is at least 80% identical to nucleic acid sequence selected from the group consisting of SEQ ID NO:1, SEQ ID NO:4, SEQ ID NO:7, SEQ ID NO:10 and SEQ ID NO:13.

One embodiment is a nucleic acid molecule comprising a nucleic acid sequence that is at least 85% identical to nucleic acid sequence selected from the group consisting of SEQ ID NO:1, SEQ ID NO:4, SEQ ID NO:7, SEQ ID NO:10 and SEQ ID NO:13. One embodiment is a nucleic acid molecule comprising a nucleic acid sequence that is at least 90% identical to nucleic acid sequence selected from the group consisting of SEQ ID NO:1, SEQ ID NO:4, SEQ ID NO:7, SEQ ID NO:10 and SEQ ID NO:13. One embodiment is a nucleic acid molecule comprising a nucleic acid sequence that is at least 95% identical to nucleic acid sequence selected from the group consisting of SEQ ID NO:1, SEQ ID NO:4, SEQ ID NO:7, SEQ ID NO:10 and SEQ ID NO:13. In each of these inventions, the AQP-1 protein encoded by the respective nucleic acid molecule retains the ability to form a channel that allows the passage of water.

Vectors and Virions

Adeno-associated virus (AAV) is a unique, non-pathogenic member of the Parvoviridae family of small, non-enveloped, single-stranded DNA animal viruses. AAV require helper virus (e.g., adenovirus) for replication and, thus, do not replicate upon administration to a subject. AAV can infect a relatively wide range of cell types and stimulate only a mild immune response, particularly as compared to a number of other viruses, such as adenovirus. A number of AAV serotypes have been identified. Examples include AAV1, AAV2, AAV3, AAV4, AAV5, AAV6, AAV7, AAV8, AAV9, AAV10, AAV11, and AAV12, which appear to be of simian or human origin. AAV have also been found in other animals, including birds (e.g., avian AAV, or AAAV), bovines (e.g., bovine AAV, or BAAV), canines, equines, ovines, and porcines.

AAV vectors are recombinant nucleic acid molecules in which at least a portion of the AAV genome is replaced by a heterologous nucleic acid molecule. The DNA from any AAV of the present invention can be used to construct an AAV vector. One example of an AAV1 genome is Genbank Accession No. AF063497. One example of an AAV2 genome is NCBI Reference No. NC_001401.2. One example of an AAV3 genome is NCBI Accession No. NC_001729.1. One example of an AAV4 genome is Genbank Accession No. U89790. One example of an AAV5 genome is Genbank Accession No. AF085716. One example of an AAV6 genome is Genbank Accession No. AF028704.1. One example of an AAV7 genome is Genbank Accession No. AF513851. One example of an AAV8 genome is Genbank Accession No. AF513852. One example of an AAV9 genome is Genbank Accession No. AY530579. One example of an AAV10 genome is Genbank Accession No. AY631965. One example of an AAV11 genome is Genbank Accession No. AY631966. One example of an AAV12 genome is Genbank Accession No. DQ813647.1. One example of a BAAV genome is Genbank Accession No. AY388617.1. One example of an AAAV genome is Genbank Accession No. AY186198.1

It is possible to replace about 4.7 kilobases (kb) of AAV genome DNA, e.g., by removing the viral replication and capsid genes. Often the heterologous nucleic acid molecule is simply flanked by AAV inverted terminal repeats (ITRs) on each terminus. The ITRs serve as origins of replication and contain cis acting elements required for rescue, integration, excision from cloning vectors, and packaging. Such vectors typically also include a promoter operatively linked to the heterologous nucleic acid molecule to control expression.

An AAV vector can be packaged into an AAV capsid in vitro with the assistance of a helper virus or helper functions expressed in cells to yield an AAV virion. The serotype and cell tropism of an AAV virion are conferred by the nature of the viral capsid proteins.

AAV vectors and AAV virions have been shown to transduce cells efficiently, including both dividing and non-dividing cells. AAV vectors and virions have been shown to be safe and to lead to long term in vivo persistence and expression in a variety of cell types.

As used herein, an AAV vector that encodes an AQP-1 protein is a nucleic acid molecule that comprises: a nucleic acid molecule encoding an AQP-1 protein of the invention, an ITR joined to 5' terminus of the AQP-1 nucleic acid molecule, and an ITR joined to the 3' terminus of the AQP-1 nucleic acid molecule. Examples of ITRs include, but are not limited to, AAV1, AAV2, AAV3, AAV4, AAV5, AAV6, AAV7, AAV8, AAV9, AAV10, AAV11, AAV12, AAAV, BAAV, and other AAV ITRs known to those skilled in the art. In one embodiment, an AAV ITR is selected from AAV2 ITR, AAV5 ITR, AAV6 ITR, and BAAV ITR. In one embodiment, an AAV ITR is an AAV2 ITR. In one embodiment, an AAV ITR is an AAV5 ITR. In one embodiment, an AAV ITR is an AAV6 ITR. In one embodiment, an AAV ITR is a BAAV ITR.

An AAV vector of the invention can also include other sequences, such as expression control sequences. Examples of expression control sequences include, but are not limited to, a promoter, an enhancer, a repressor, a ribosome binding site, an RNA splice site, a polyadenylation site, a transcriptional terminator sequence, and a micro RNA binding site. Examples of promoters include, but are not limited to, an AAV promoter, such as a p5, p19 or p40 promoter, an adenovirus promoter, such as an adenoviral major later promoter, a cytomegalovirus (CMV) promoter, a papilloma virus promoter, a polyoma virus promoter, a respiratory syncytial virus (RSV) promoter, a sarcoma virus promoter, an SV40 promoter, other viral promoters, an actin promoter, an amylase promoter, an immunoglobulin promoter, a kallikrein promoter, a metallothionein promoter, a heat shock promoter, an endogenous promoter, a promoter regulated by rapamycin or other small molecules, other cellular promoters, and other promoters known to those skilled in the art. In one embodiment, the promoter is an AAV promoter. In one embodiment, the promoter is a CMV promoter. Selection of expression control sequences to include can be accomplished by one skilled in the art.

The disclosure provides AAV vectors of different serotypes (as determined by the serotype of the ITRs within such vector) that encode an AQP-1 protein of the invention. Such an AAV vector can be selected from an AAV1 vector, an AAV2 vector, an AAV3 vector, an AAV4 vector, an AAV5 vector, an AAV6 vector, an AAV7 vector, an AAV8 vector, an AAV9 vector, an AAV10 vector, an AAV11 vector, an AAV12 vector, an AAAV vector, and a BAAV vector, wherein any of such vectors encode an AQP-1 protein of the invention. One embodiment is an AAV2 vector, an AAV5 vector, an AAV6 vector or a BAAV vector, wherein the respective vector encodes an AQP-1 protein of the invention. One embodiment is an AAV2 vector that encodes an AQP-1 protein of the invention. One embodiment is an AAV5 vector that encodes an AQP-1 protein of the invention. One embodiment is an AAV6 vector that encodes an AQP-1 protein of the invention. One embodiment is a BAAV vector that encodes an AQP-1 protein of the invention.

One embodiment is an AAV vector that comprises AAV ITRs and a CMV promoter operatively linked to a nucleic acid molecule encoding an AQP-1 protein of the invention.

One embodiment is an AAV vector that comprises AAV ITRs and a CMV promoter operatively linked to a nucleic acid molecule encoding an AQP-1 fusion protein of the invention. One embodiment is an AAV2 vector that comprises AAV2 ITRs and a CMV promoter operatively linked to a nucleic acid molecule encoding an AQP-1 protein of the invention. One embodiment is an AAV2 vector that comprises AAV2 ITRs and a CMV promoter operatively linked to a nucleic acid molecule encoding an AQP-1 fusion protein of the invention.

One embodiment is an AAV vector that has the nucleic acid sequence of SEQ ID NO:18.

The disclosure provides plasmid vectors that encode an AQP-1 protein of the invention. Such plasmid vectors also include control regions, such as AAV ITRs, a promoter operatively linked to the nucleic acid molecule encoding the AQP-1 protein, one or more splice sites, a polyadenylation site, and a transcription termination site. Such plasmid vectors also typically include a number of restriction enzyme sites as well as a nucleic acid molecule that encodes drug resistance.

The present invention also provides an AAV virion. As used herein, an AAV virion is an AAV vector encoding an AQP-1 protein of the invention encapsidated in an AAV capsid. Examples of AAV capsids include AAV1 capsids, AAV2 capsids, AAV3 capsids, AAV4 capsids, AAV5 capsids, AAV6 capsids, AAV7 capsids, AAV8 capsids, AAV9 capsids, AAV10 capsids, AAV11 capsids, AAV12 capsids, AAAV capsids, BAAV capsids, and capsids from other AAV serotypes known to those skilled in the art. In one embodiment, the capsid is a chimeric capsid, i.e., a capsid comprising VP proteins from more than one serotype. As used herein, the serotype of an AAV virion of the invention is the serotype conferred by the VP capsid proteins. For example, an AAV2 virion is a virion comprising AAV2 VP1, VP2 and VP3 proteins. Any AAV virion can be used to practice the methods of the invention so long as the virion is capable of efficiently transducing ductal or acinar cells.

One embodiment of the disclosure is an AAV virion selected from an AAV2 virion, an AAV5 virion, an AAV6 virion, and a BAAV virion, wherein the AAV vector within the virion encodes an AQP-1 protein of the present invention. One embodiment is an AAV2 virion, wherein the AAV vector within the virion encodes an AQP-1 protein of the present invention. One embodiment is an AAV5 virion, wherein the AAV vector within the virion encodes an AQP-1 protein of the invention. One embodiment is an AAV6 virion, wherein the AAV vector within the virion encodes an AQP-1 protein of the invention. One embodiment is a BAAV virion, wherein the AAV vector within the virion encodes an AQP-1 protein of the invention.

Methods useful for producing AAV vectors and AAV virions disclosed herein are known to those skilled in the art and are also exemplified in the Examples. Briefly, an AAV vector of the present invention can be produced using recombinant DNA or RNA techniques to isolate nucleic acid sequences of interest and join them together as described herein, e.g., by using techniques known to those skilled in the art, such as restriction enzyme digestion, ligation, PCR amplification, and the like. Methods to produce an AAV virion of the invention typically include (a) introducing an AAV vector of the invention into a host, (b) introducing a helper vector into the host cell, wherein the helper vector comprises the viral functions missing from the AAV vector and (c) introducing a helper virus into the host cell. All functions for AAV virion replication and packaging need to be present, to achieve replication and packaging of the AAV vector into AAV virions. In some instances, at least one of the viral functions encoded by the helper vector can be expressed by the host cell. Introduction of the vectors and helper virus can be carried out using standard techniques and occur simultaneously or sequentially. The host cells are then cultured to produce AAV virions, which are then purified using standard techniques, such as CsCl gradients. Residual helper virus activity can be inactivated using known methods, such as heat inactivation. Such methods typically result in high titers of highly purified AAV virions that are ready for use. In some invention, an AAV vector of a specified serotype is packaged in a capsid of the same serotype. For example, an AAV2 vector can be packaged in an AAV2 capsid. In other invention, an AAV vector of a specified serotype is packaged in a capsid of a different serotype in order to modify the tropism of the resultant virion. Combinations of AAV vector serotypes and AAV capsid serotypes can be determined by those skilled in the art.

Compositions and Methods of Use

The disclosure provides a composition comprising an AAV vector encoding an AQP protein of the present invention, such as AQP-1 or an AQP-5 protein of the present invention. The disclosure also provides a composition comprising an AAV virion comprising an AAV vector encoding an AQP protein, such as an AQP-1 or an AQP-5 protein of the invention. Such compositions can also include an aqueous solution, such as a physiologically compatible buffer. Examples of excipients include water, saline, Ringer's solution, and other aqueous physiologically balanced salt solutions. In some invention, excipients are added to, for example, maintain particle stability or to prevent aggregation. Examples of such excipients include, but are not limited to, magnesium to maintain particle stability, pluronic acid to reduce sticking, mannitol to reduce aggregation, and the like, known to those skilled in the art.

A composition of the invention is conveniently formulated in a form suitable for administration to a subject. Techniques to formulate such compositions are known to those skilled in the art. For example, an AAV vector or virion of the invention can be combined with saline or other pharmaceutically acceptable solution; in some embodiments excipients are also added. In another embodiment, a composition comprising an AAV vector or virion is dried, and a saline solution or other pharmaceutically acceptable solution can be added to the composition prior to administration.

The disclosure provides a method to protect a subject from Sjögren's syndrome-related xerostomia. Such a method includes the step of administering to the subject a vector of the invention. Such a vector will encode an AQP-1 or an AQP5 protein of the invention. Any method of administration can be used, so long as the vector is taken up into cells, and in particular, ductal and acinar cells. Examples of such methods include, but are not limited to, transduction of cells using naked DNA, which includes lipid-encapsulated DNA, delivery into cells using recombinant viruses, and delivery into cells using minicells (see, for example, U.S. Patent Publication No. 20030199088). With regard to the use of viruses, any virus that is capable of delivering the AQP-1 or the AQP-5 gene into a cell, thereby resulting in expression of the corresponding AQP protein, can be used.

One example of a useful virus is an adeno-associated virus (AAV). One embodiment is an AAV virion comprising an AAV vector that encodes an AQP-1 or AQP-5 protein of the invention. As used herein, the ability of an AAV virion of the invention to protect a subject from Sjögren's syndrome-related xerostomia or Sjögren's syndrome-related xeropthalmia refers to the ability of such AAV virion to prevent, treat, or ameliorate symptoms of Sjögren's syndrome-related xerostomia or Sjögren's syndrome-related xeropthalmia. According to the present invention, treating symptoms xerostomia or xeropthalmia may refer to completely eliminating symptoms or partially eliminating symptoms. That is, treating, or protecting an individual from symptoms, refers to restoring the physiological state of the individual to a clinically acceptable level. For example, with regard to the flow of saliva or tears, methods of the present invention may return such flow to 70%, 80%, 85%, 90%, 05% or 00% of the value observed in a normal individual (i.e., individual known to be free of Sjögren's syndrome).

In one embodiment, an AAV virion of the invention prevents symptoms of Sjögren's syndrome-related xerostomia or Sjögren's syndrome-related xeropthalmia. In one embodiment, an AAV virion of the invention treats symptoms of Sjögren's syndrome-related xerostomia or Sjögren's syndrome-related xeropthalmia. In one embodiment, an AAV virion of the invention ameliorates symptoms of Sjögren's syndrome-related xerostomia or Sjögren's syndrome-related xeropthalmia. In one embodiment, an AAV virion of the invention prevents symptoms of Sjögren's syndrome-related xerostomia or Sjögren's syndrome-related xeropthalmia from occurring in a subject, for example in a subject susceptible to Sjögren's syndrome-related xerostomia or Sjögren's syndrome-related xeropthalmia. In one embodiment, an AAV virion of the invention prevents symptoms of Sjögren's syndrome-related xerostomia or Sjögren's syndrome-related xeropthalmia from worsening. In one embodiment, an AAV virion of the invention reduces symptoms of Sjögren's syndrome-related xerostomia or Sjögren's syndrome-related xeropthalmia in a subject. In one embodiment, an AAV virion of the invention enables a subject to recover from symptoms of Sjögren's syndrome-related xerostomia or Sjögren's syndrome-related xeropthalmia. Sjögren's syndrome-related xerostomia can lead to a number of symptoms including, but not limited to the following: reduced salivary function, which can result in xerostomia (dry mouth); reduced lachrymal gland function, which can result in xerophthalmia (conjunctivitis sicca, dry eyes); immune cell infiltration (e.g., T cells, B cells, macrophages) of salivary glands; immune cell infiltration of lachrymal glands; increase in proinflammatory cytokines (e.g., Th1-cell cytokines, Th17-cell cytokines); decrease in nTreg cytokines, increase in circulating autoantibodies such as antinuclear antibodies (ANA), SSA antibodies (e.g., SSA/Ro), SSB antibodies (e.g., SSB/La), and M3R antibodies; and fatigue. Methods to measure the presence or severity of such symptoms are known to those skilled in the art.

Because administration of vectors of the present invention to salivary gland cells produces a systemic effect, such administration may be used as a method to treat or protect against other symptoms of Sjögren's syndrome such as reduced lachrymal gland function (xeropthalmia). Thus, one embodiment of the present invention is a method to protect a subject from or treat reduced lachrymal (lacrimal) gland function. Such a method includes the step of administering to the subject a vector of the invention. Such a vector will encode an AQP protein of the invention such as an AQP-1 or AQP-5 protein of the invention. Because administration results in a systemic effect, the vector need not be administered to lachrymal cells. Any method of administration can be used, so long as the vector is taken up into cells, and in particular, ductal and acinar cells. Examples of such methods include, but are not limited to, transduction of cells using naked DNA, which includes lipid-encapsulated DNA, delivery into cells using recombinant viruses, and delivery into cells using minicells. With regard to the use of viruses, any virus that is capable of delivering the AQP5 gene into a cell, thereby resulting in expression of AQP protein, can be used.

As has been discussed, Sjögren's syndrome, and its related symptoms, is the results of an autoimmune attack on cells of the exocrine glands. Moreover, as demonstrated in the Examples, administration of vectors of the present invention to salivary gland cells results in a reduction in such immune response. Thus, one embodiment of the present invention is a method to reduce or eliminate an autoimmune response to exocrine gland cell antigens. Such a method includes the step of administering to the subject a vector of the invention. Such a vector will encode an AQP-1 protein of the invention. Any method of administration can be used, so long as the vector is taken up into cells, and in particular, ductal and acinar cells.

The disclosure provides a method comprising administering an AAV virion comprising an AAV vector that encodes an AQP protein to a subject, wherein such administration maintains salivary gland function in such a subject. As used herein, maintaining salivary gland function means that salivary gland function after administration of an AAV virion of the invention to a subject is equivalent to salivary gland function in that subject prior to administration of the AAV virion; for example, in the case of a subject with normal salivary gland function, the function remains normal after AAV virion administration; if the subject has symptoms, the salivary gland function does not worsen after administration of the AAV virion, but is equivalent to function prior to AAV virion administration. Also provided is a method comprising administering AAV virion comprising an AAV vector that encodes an AQP-1 protein of the invention to a subject, wherein such administration improves salivary gland function in such a subject. The disclosure provides a method comprising administering an AAV virion comprising an AAV vector that encodes an AQP-1 protein of the invention to a subject, wherein such administration maintains lachrymal gland function in such a subject. Also provided is a method comprising administering an AAV virion comprising an AAV vector that encodes an AQP-1 protein of the invention to a subject, wherein such administration improves lachrymal gland function in such a subject. As used herein, a subject is any animal that is susceptible to Sjögren's syndrome. Subjects include humans and other mammals, such as cats, dogs, horses, other companion animals, other zoo animals, lab animals (e.g., mice), and livestock.

An AAV virion of the invention can be administered in a variety of routes. In some embodiments, an AAV virion is administered by aerosol. In some embodiments, an AAV virion is administered to the mucosa. In some embodiments, an AAV virion is administered directly to a tissue or organ. In some embodiments, an AAV virion of the invention is administered to a salivary gland. In some embodiments, an AAV virion of the invention is administered to a lachrymal gland.

The disclosure also provides a method to protect a subject from Sjögren's syndrome-related xerostomia in which an AAV vector or virion of the invention is administered to a lachrymal gland of the subject. In one embodiment, a vector or an AAV1, an AAV2, an AAV3, an AAV4, an AAV5, an AAV6, an AAV7, an AAV8, an AAV9, an AAV10, an AAV11, an AAV12, an AAAV, or a BAAV of the invention is administered to a lachrymal gland.

The disclosure also provides ex vivo methods to protect a subject from Sjögren's syndrome-related xerostomia. Such methods can involve administering an AAV vector or virion of the invention to a cell, tissue, or organ outside the body of the subject, and then placing that cell, tissue, or organ into the body. Such methods are known to those skilled in the art.

The dose of compositions disclosed herein to be administered to a subject to be effective (i.e., to protect a subject from Sjögren's syndrome-related xerostomia) will depend on the subject's condition, manner of administration, and judgment of the prescribing physician. Often a single dose can be sufficient; however, the dose can be repeated if desirable. In general, the dose can range from about $10^4$ virion particles per kilogram to about $10^{12}$ virion particles per kilogram. A preferred does is in the range of from about $10^6$ virion particles per kilogram to about $10^{12}$ virion particles per kilogram. A more preferred does is in the range of from about $10^8$ virion particles per kilogram to about $10^{12}$ virion particles per kilogram.

The disclosure provides a treatment for Sjögren's syndrome-related xerostomia. Such a treatment comprises an AAV vector, or a virion comprising such a vector, that encodes an AQP-1 protein. Administration of such a treatment to a subject protects the subject from Sjögren's syndrome-related xerostomia.

The disclosure also provides a preventative for Sjögren's syndrome-related xerostomia. Such a preventative comprises an AAV vector, or a virion comprising such a vector, that encodes an AQP-1 protein. Administration of such a preventative to a subject protects the subject from Sjögren's syndrome-related xerostomia.

The disclosure provides a salivary gland cell transfected with an AAV vector that encodes an AQP-1 protein. The salivary gland cell can be that of a subject with Sjögren's syndrome. In one embodiment, the salivary gland cell is that of a subject with Sjögren's syndrome.

The disclosure provides a vector, and an AAV virion comprising such a vector, that encodes an AQP-1 protein of the invention for the treatment or prevention of Sjögren's syndrome-related xerostomia. In one embodiment, such an AAV vector or virion is useful for protecting a subject from Sjögren's syndrome. In one embodiment, such an AAV vector or virion is useful for treating a subject with Sjögren's syndrome-related xerostomia. In one embodiment, such an AAV vector or virion is useful for preventing Sjögren's syndrome-related xerostomia in a subject. The disclosure also provides for the use of an AAV vector, or a virion comprising such a vector, that encodes an AQP-1 protein of the invention for the preparation of a medicament to protect a subject from Sjögren's syndrome-related xerostomia.

EXAMPLES

The following examples are set forth so as to provide those of ordinary skill in the art with a complete disclosure and description of how to make and use the invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Efforts have also been made to ensure accuracy with respect to nucleic acid sequences and amino acid sequences presented, but some experimental errors and deviations should be accounted for. Unless indicated otherwise, parts are parts by weight, molecular weight is weight average molecular weight, and temperature is in degrees Celsius. Standard abbreviations are used.

Example 1

Expression Profile of BMP-6 Receptors ACVR1A and BMPR1A

Bone morphogenic protein 6 (BMP-6), like the other BMP members, signals through ligation and heterodimerization of BMP type I (ACVR1A) and type II serine-threonine kinase (BMPR1A) receptors, which subsequently propagate the signal downstream by phosphorylating Smad proteins. The phosphorylated Smad receptors are then translocated into the nucleus where they affect gene regulation. Analysis of the role of BMP-6 in the regulation of human salivary gland function was first conducted by immune-fluorescent analysis of BMPR1A and ACVR1A receptors for BMP-6 in a human salivary gland cell line (HSG) and in human salivary gland tissue. Briefly, the HSG cell line was cultured with 1× Minimum Essential Medium (GIBCO) containing 10% of FBS (Invitrogen) and 1% antibiotics at 37° C. in 5% $CO_2$. The cells were then washed with PBS, fixed using 4.0% formalin, 4.0% of formalin (37° C.) for 5 min and immediately washed by warmed PBS buffer at 37° C. The cells were then stained using antibodies specific for ACVR1A and BMPR1A according to the manufacturer's instructions.

For immune-fluorescent analysis of human salivary gland tissue, submandibular glands (SMG) tissues were removed and fixed using 10% formalin. After fixation, the tissues were dehydrated using ethanol, embedded in paraffin according standard techniques and 5 μm sections cut. The sections were washed using PBS buffer and stained with specific antibodies for the BMP-6 receptors, ACVR1A and BMPR1A.

Confocal imaging of the stained cells and salivary tissue showed that BMPR1A and ACVR1A were detected in both the human salivary gland cell line HSG and on ductal cells in human salivary gland tissue.

Example 2

Inhibition of Hypotonic-Induced Swelling of Human Salivary Gland Cells

This example demonstrates the ability of BMP6 to inhibit hypotonic-induced swelling of human salivary gland cells.

The regulation of cell volume is an essential function coupled to a variety of physiological processes, such as cell proliferation, differentiation, iron or water secretion and migration. Even under hypotonic stress imposed by either decreased extracellular or increased intracellular osmolarity, cells can adjust their volume after transient osmotic swelling by a mechanism known as regulatory volume decrease (RVD). Under patho-physiological conditions, cells often undergo a persistent swelling or shrinkage without showing volume regulation. Such impaired volume regulation is coupled to the initial steps of necrotic and apoptotic cell death. Thus, the ability of BMP-6 to mediate inhibition of RVD in HSG cells was examined Briefly, HSG cells were cultures as described in Example 1. Recombinant human BMP-6 (R&D System), diluted in 1 mM Tris-HCl buffer containing 0.1% bovine serum albumin or human serum albumin, and stored at −20° C. until use, was added into the cultures of HSG cells for 4 days at concentration of 0.1 ng/ml, 6 ng/ml, or 150 ng/ml. After treatment with BMP-6, regulated volume decrease (RVD) was measured as described by Lui et al., *Journal of Biological Chemistry* 281, 15485-15495 (2006). Briefly, isolated cells were loaded with the fluoroprobe calcein (Molecular Probes, Inc., Eugene, Oreg.), excited at 490 nm and the emitted fluorescence measured at 510 nm. The affect of varying concentrations of BMP-6 on RVD was examined next. Briefly, HSG cells loaded with the fluoro-probe calcein (Molecular Probes, Inc., Eugene, Oreg.) and excited at 490 nm. Emitted fluorescence was measured at 510 nm (22). In situ calibration of the dye was performed. The relationship between dye fluorescence and the volume change was linear over a volume range from +35 to −355. The cell volume was estimated using an Olympus X51 microscope interfaced with Universal Imaging MetaMorph software. The results of this analysis are shown in FIG. 1 and demonstrate that BMP-6 induces inhibition of RVD in HSG cells with a dose dependent manner.

Example 3

BMP-6 Induced Changes in Gene Expression

To identify changes in gene expression associated with BMP-6 induced loss of RVD, the BMP6 responsive transcriptome was mapped. Briefly HSG cells were cultured as described in Example 1. The cultured cells were then treated with varying concentrations of BMP-6 as described in Example 2. Following treatment with BMP-6, total RNA was extracted with an RNeasy Mini Kit (Qiagen) according to the manufacturer's recommendation and analyzed using a microarray. Briefly, 550 µl of RNA Nano gel was loaded into a spin filter and centrifuge at 1500 g for 10 min at room temperature; and 65 µl of the gel was mixture with 1 µl of Nano 6000 dye and centrifugation at 13000 g for 10 min at RT, 9.0 µl of this gel-dye mix will then loaded into 3 wells marked with G of the RNA Nano Chips (Agilent) and 5.0 µl of RNA 6000 Nano Market was loaded into all 12 samples wells, subsequently, 1.0 µl of samples was added into the same each of the 12 samples wells. The chip was then placed horizontally in the adapter of the IKA vortexes and vortex for 1 min before its loading into the Agilent 2100 bioanalyzer. Total RNA from both of patient samples and the control samples were amplified and labeled with a lower RNA input linear amplification kit (Agilent). A total of 500 ng RNA was labeled with Cyanine 3-CTP according to the manufacturer's instructions; briefly, 500 ng of total RNA was first mixed with 2.0 µl of RNA spike (One-Color Spike, Agilent) previously diluted by a series of concentrations of 1:20, 1:25 and 1:10 in a 1.5 ml tube including T7 primer that was incubated at 65° C. for 10 min. The reaction temperature was changed to 40° C. after adding 8.5 ul of cDNA Master Mix reagents (Agilent) for 2 hours, and the samples were moved to a 65° C. circulating water bath additional incubate for 15 min, and quench in ice for 5 min The reaction was subsequently to 60 µl of the Transcription Master Mix including Cyanine 3-CTP (Agilent) for each sample for additional 5 hours at 40° C. The labeled and amplified cRNA was purified by using a kit of RNeasy Mini Kit (Qiagen). The quality and yield of cRNA were then analyzed with use of NanoDropt ND-1000 UV-VIS Spectrophoometer (version 3.2.1). Only cRNA with a total yield>1.65 µg and the specific avidity>9.0 pmol Cy3 per µg cRNA were used in the hybridization step. Microarrays were hybridized according to the manufacturer's recommendations from One-Color Microarray-Based Gene Expression Analysis (Agilent). Briefly, each tube containing reaction reagents: 1.65 µg of new Cy3-labelled cRNA, 11 ul of 10× blocking agent (Agilent) and 2.2 µl of 25× Fragment buffer (Agilent) was incubated at 60° C. for exactly 30 min and then 55 µl of 2×GE×Hybridization buffer (Agilent) was added to stop the fragmentation reaction. Following centrifuge at room temperature (table top 13,000 rpm for 1 min), 100 µl of the sample solution was loaded onto each array on the slides that was then assembled in the hybridization chamber (Agilent). The final assembled slide chamber was placed in a hybridization oven with rotating speed of 10 rpm at 65° C. for 17 hours. After disassemble of array hybridization chambers, the slides are placed in dish #1 with Gene Expression Wash Buffer-1 (Agilent) and washed for 1 min at room temperature. From the Wash buffer-1 dish, the slides were then directly transferred into dish #2 with pre-warmed (37° C.) Gene Expression Wash Buffer-2 (Agilent). Following the washing procedure, the slides were immediately scanned using a Microarray Scanner (Model: Agilent G2565AA System) to minimize the environmental oxidation and loss of signal intensities. The microarray data (.tif images) file was extracted using the Agilent Feature Extraction (FE) (software version 9.5.1) program, for One-color gene expression, the default gene expression is specified in the FE grid template properties with selection of "GE1_QCM_Feb07" in this protocol. After the extraction is completed, the QC (quality control) report with a summary table of metric values are viewed and analyzed including determining whether the grid has been properly placed by inspecting Spot Finding at the Four Corners of the Array. Those chips that meet with the requirement of QC reports (9 evaluation criteria from a table of "Evaluation Metrics for GE1_QCM-Feb07" are used) are selected for further data statistics in the following.

Figure 2:
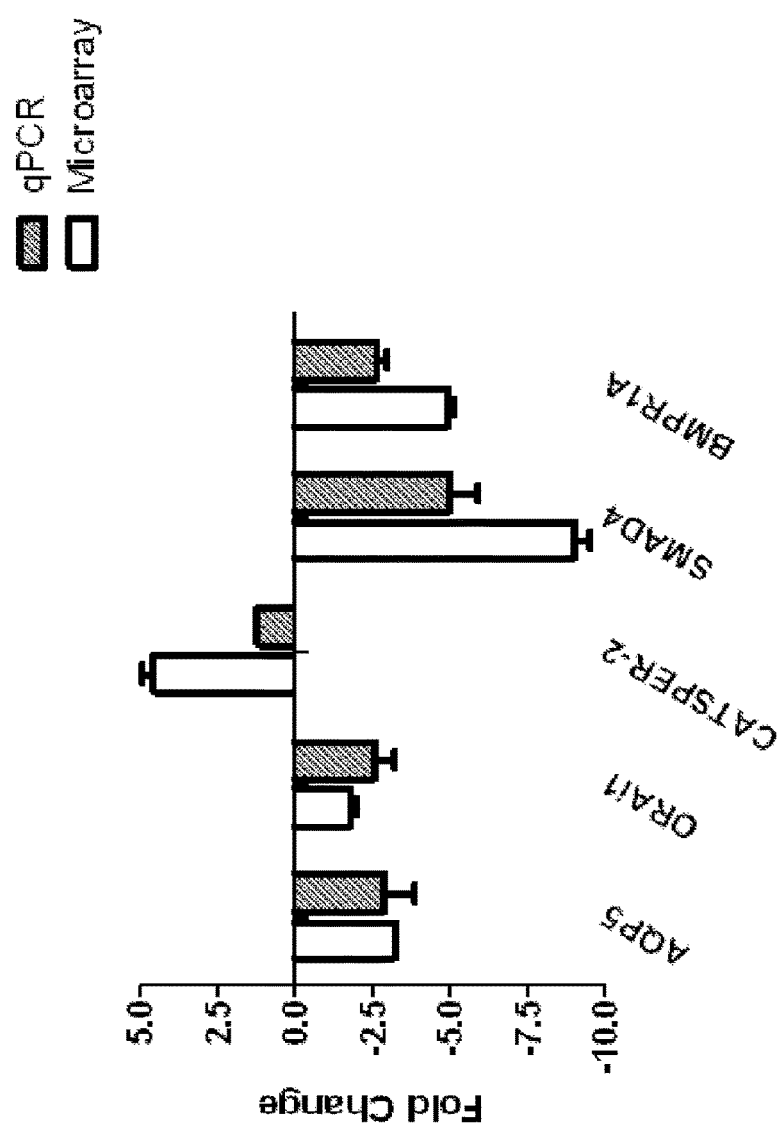
FIG. 2. Quantitative-PCR of selected genes. Quantitative-PCR of selected genes extracted from HSG cells after BMP-6 treatment that shows agreement with the results of microarray study on the samples from patients with Sjögren's syndrome. The results obtained using the custom microarray platform was validated by examining the correlation between the expression levels in the microarray and qPCR results obtained for a subset of genes. The data are averaged over at least two independent experiments.

The results of this analysis, indicate that different dosages of BMP-6 are able to induce different response patterns of the gene expression levels. Several of the gene changes observed were verified by QPCR (FIG. 2). Total human RNA (500 ng) was reverse transcribed using a SuperScript (VLO™) First-Strand cDNA synthesis kit according to the manufacture instruction (Invitrogen). The reaction component are 10× SuperScript Enzyme mix and 5×VILO Reaction Mix with including random primers, $MgCl_2$, and dNTPs, and the tubes were subjected into a PCR program of 25° C. for 10 min, 42° C. for 60 min and 85° C. for 5 min. The final samples of $1^{st}$ strand cDNA are stored at −20° C. until use for real-time PCR. Expression was further validated by QPCR using a (2×) Taqman Universal PCR Master Mix (Applied Biosystem Inc). The cDNA was diluted as final concentration of 1.0 ng/µl. The $1^{st}$ strand of the cDNA synthesized from human total RNA was used as template for real-time PCR. The reaction was carried out on an optional tube including 10 ng of the synthesized cDNA, 1.0 µl of TaqMan Probes and 10 µl of a (2×) Universal PCR Master Mix (Applied Biosystem) containing AmpliTaq DNA polymerase, uracil-DNA glycosylase, dNTPs/dUTP, ROX™ positive reference and optimized buffer components that were purchased from Applied Biosystem with a total final volume of 20 µl. The real-time PCR reaction was run on the Instrument (ABI PRISM).

Example 4

Changes in Gene Expression in BMP-6 Treated Mice

To further explore gene expression changes induced by BMP-6, additional microarray data was developed for mice treated with BMP6 in vivo following salivary gland targeted treatment with AAV5 vectors encoding BMP6. The construction of the AAV5 BMP6 vectors have been described in Li et al Tissue Eng. 2006 February; 12(2):209-19. Vectors were delivered into the submandibular glands by retrograde instillation as previously described by (20) Briefly, mild anesthesia was induced by ketamine (100 mg/mL, 1 mL/kg body weight (BW); Fort Dodge Animal Health, Fort Dodge, Iowa, USA) and xylazine (20 mg/mL, 0.7 mL/kg body weight; Phoenix Scientific, St. Joseph, Mo., USA) solution given intramuscularly (IM). Ten minutes after IM injection of atropine (0.5 mg/kg BW; Sigma, St. Louis, Mo., USA), Aec1/Aec2 mice at the age of 30 weeks were administered 50 µl vector into both submandibular glands by retrograde ductal instillation ($1\times10^{10}$ particles/gland) using a thin cannula (Intermedic PE10, Clay Adams, Parsippany, N.J., USA). The vector dose was chosen based on previously published results, which showed detectable transgene activity above $10^9$ particles/gland (21). The mouse salivary glands were collected, their RNAs extracted (as described in Example (2) and changes in gene expression identified by microarray analysis as described in Example 2.

The results of this analysis, listed in Table 2, identified a number of genes that correlated with the change in RVD activity. In this analysis, AQP-5 showed the most significant change in expression.

reduction in the density of AQP-5 cells in the cell membrane when compared with untreated cells.

Example 6

Recovery of RVD by Complementation with AQP

To confirm the role of AQP5 in the BMP6 induced loss of RVD in HSG cells, an AQP5 or AQP1 encoding plasmid was transfected into HSG cells pre-treated with BMP-6. Briefly, 6-well plates containing HSG cells were grown to 70-90% confluent, then transfected by using LIPOFECTAMINE™ 2000 according to the manufactures instruction (Invitrogen); the cells were changed with new growth medium without antibiotics prior to transfection. A total of 4.0 µg of DNA of either AAV2-AQP5 or AAV2-AQP-1, was combined with a reporter plasmid encoding green-fluorescent protein (GFP) as a transfection control, and puc19 as a carrier plasmid in 50 µl of OPTI-MEM™ Reduced Serum (Invitrogen) was mixed with 50 µl diluted reagent of LIPOFECTAMINE™ 2000 (10 µl per well) after incubation for 5 minutes at room temperature. The 100 µl of final mixture solution after incubation for 20 minutes at room temperature was added into the each well of HSG cells, and changed with growth medium after 4-6 hours. The transfected HSG cells were then incubated at 37° C. in a $CO_2$ incubator for 18-48 hours

TABLE 2

Genes correlated with the change in RVD activity.

| Symbol | Entrez Gene Name | Location | Family | 0.1 ng BMP | 6 ng BMP6 | 150 ng BMP6 | BMP6 mice |
|---|---|---|---|---|---|---|---|
| | | | | | Fold Change | | |
| AQP5 | Aquaporin 5 | Plasma Membrane | Transporter | −1.458 | −7.156 | | −1.896 |
| COX7B | Cytochrome oxidase subunit VIIb | Cytoplasm | Enzyme | 1.299 | 1.747 | | 1.278 |
| ERG1 | Early growth response1 | Nucleus | Transcription regulator | 2.049 | 4.211 | | 1.16 |
| FAT1 | FAT tumor suppressor homolog 1 (Drosophila) | Plasma Membrane | Other | 1.450 | 1.821 | | 1.864 |
| IGSF10 | Immunoglobulin superfamily, member10 | Unknown | Other | −1.388 | −2.580 | | −1.216 |
| NKRF | NKB repressing factor | Nucleus | Transcription regulator | 1.469 | 1.913 | | 1.342 |
| PPP2R2A | Protein phosphatase 2, regulatory subunit B, α | Cytoplasm | phosphatase | 1.343 | 1.493 | | −1.237 |

Example 5

Immunofluorescence Analysis of BMP-6 Induced Change in Aquaporin-5 Expression

Figures 3A, 3B:
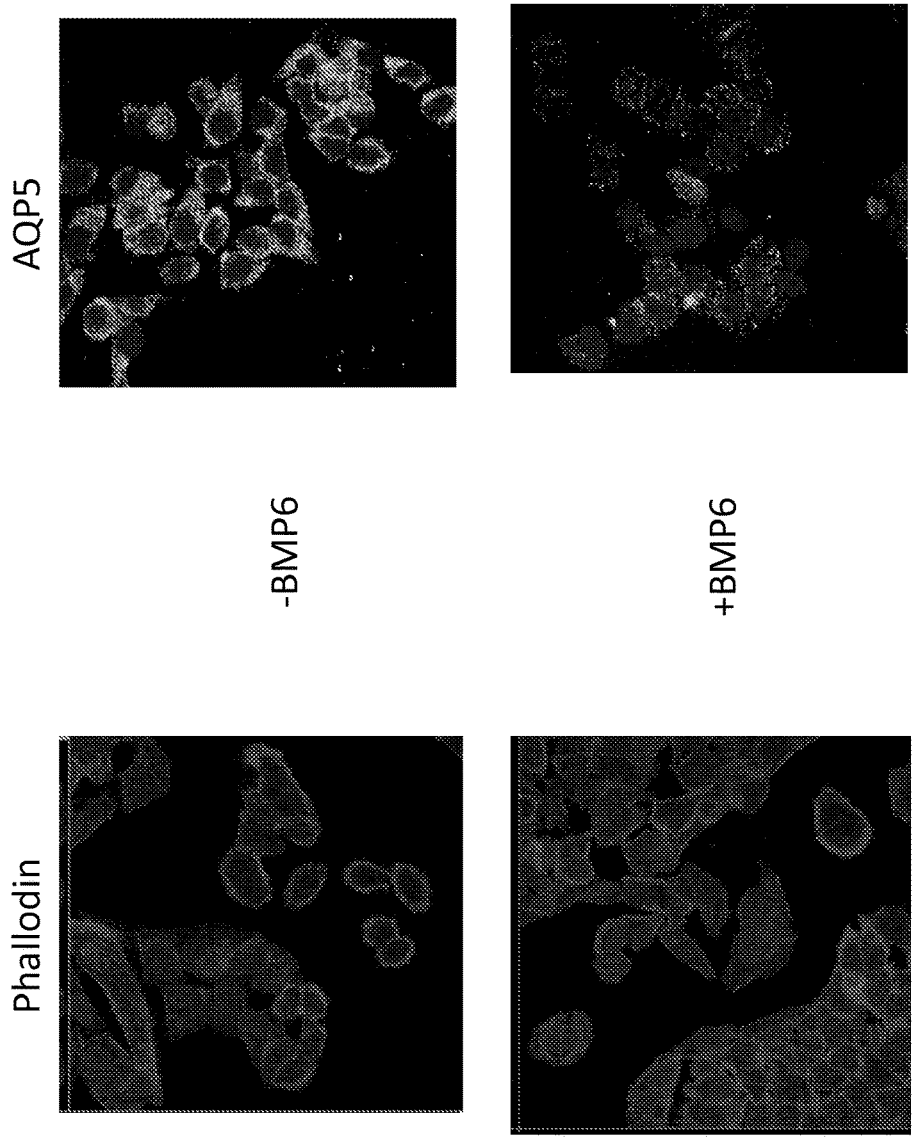
FIG. 3. Immunohistochemistry analysis of human salivary gland cells (HSG). The HSG cells were and treated with 6 ng/ml of BMP-6 for 4 days. The HSG cells washed by warming (at 37° C.) PBS buffer and were then subjected for immunohistochemistry staining by specific antibodies of anti-phallodin and anti-AQP-5. A) Phallodin conjugated to TRITC with red fluorescence was shown in the left panel. B) The specific antibody to AQP-5 conjugated to FITC with green fluorescence was shown in the right panel. (The top panel: cells without treatment of BMP-6; the bottom panel: cells treated by BMP-6).
Figure 4B:
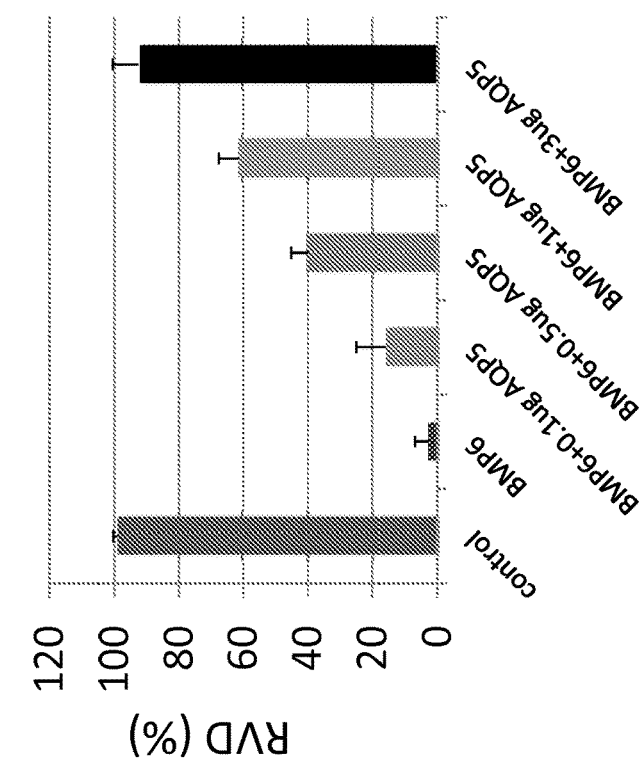
FIG. 4. AQP induces recovery of dysfunction of RVD on HSG cells treated with BMP-6. A): The HSG cells as control were incubated with HTS solution only to stimulate the RVD reaction without BMP-6 and AQP-5; the regulation of RVD in HSG cell was completely inhibited by treatment with BMP-6 (6 ng); However, the dysfunction of RVD were gradually recovered by delivery of AQP-5 with different dosages of 0.1 μg, 0.5 μg, 1.0 μg and 3.0 μg B): Dosage response curve of AQP-5 induces recovery of RVD dysfunction on HSG cell volume changed by BMP-6; data are presented as mean±S.E. C) AQP1-induced recovery of regulated volume decrease induced by addition of hypotonic solution (HTS) of 150 mOsm. Control cells are normal, human salivary gland (HSG) cells cultured in DMEM media. BMP6: Cells treated with 6 ng/ml of BMP6 for 96 hours. MBP6+AQP-1: Cells treated with BMP6 and transfected with an AAV2 vector expressing AQP-1. AQP-1: Control cells treated transfected with an AAV2 vector expressing AQP-1 alone.
Figure 4A:
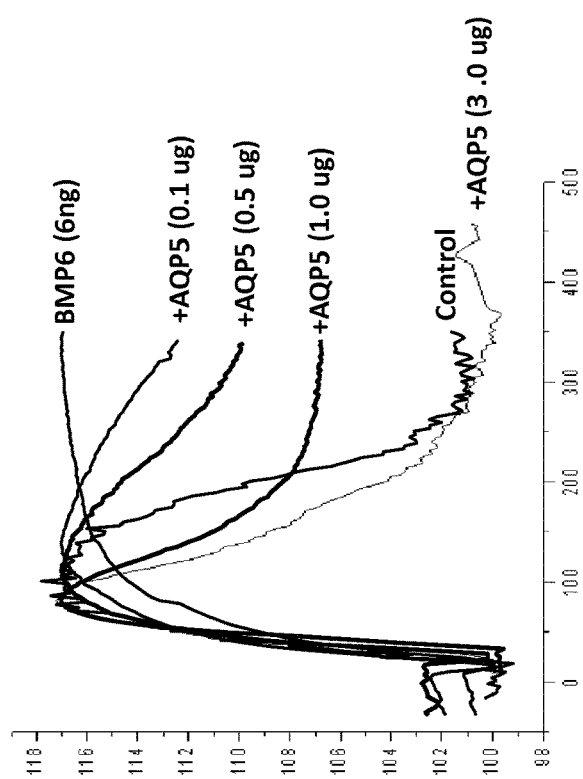
Figure 4C:
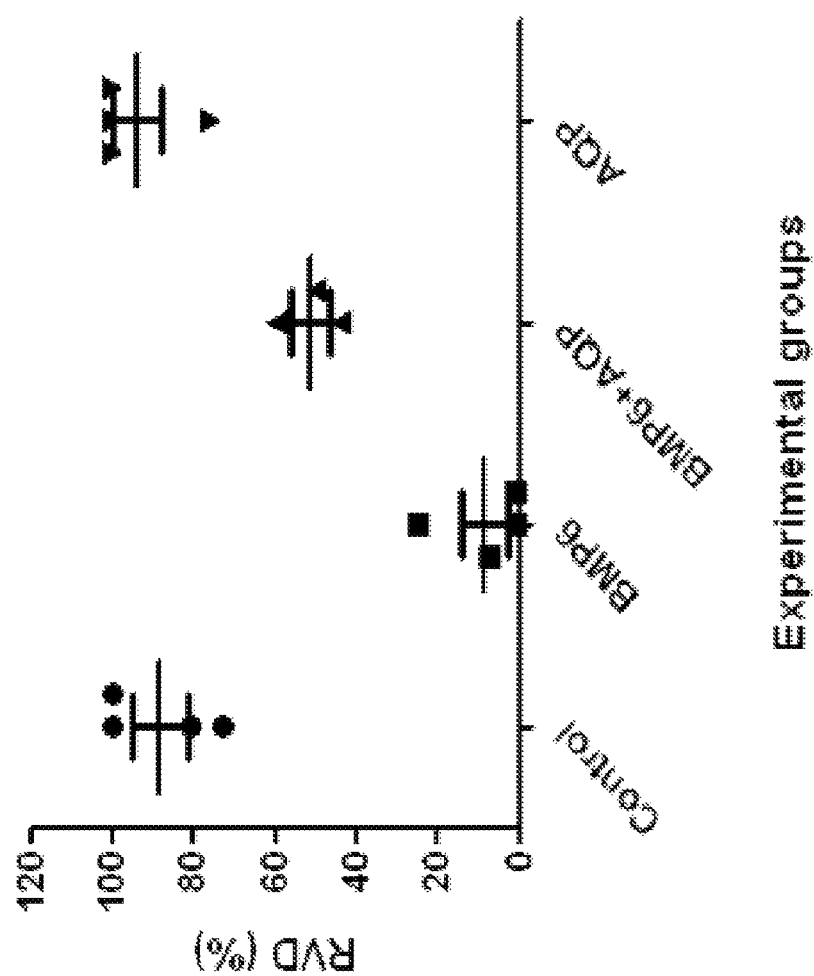

In order to further investigate the effect of BMP-6 on changes in aquaporin-5 expression, confocal imaging was performed on HSG cells treated with BMP-6. HSG cells were cultured as described in Example 1. The cultured cells were then treated with BMP-6, as described in Example 2, and stained with antibodies specific for AQP-5 according to the manufacturer's instructions. As a control, separate cultures of HSG cells, with or without BMP-6 treatment, were imaged with phalloidin, which has a high-affinity for actin. The results of this analysis, are shown in FIG. 3, demonstrate that treatment of HSG cells with BMP-6 resulted in a prior to testing for transgene expression. The results, shown in FIG. 4, demonstrate that a dose-dependent increase in RVD was observed with increasing amounts of AQP5 plasmid. Similarly, transfection with AQP1 could also rescue the loss of RVD (FIG. 4C).

Example 7

Restoration of Salivary Gland Activity in Mice

To determine whether aquaporin could restore salivary gland activity in a mouse model of Sjögren's syndrome, AAV vectors expressing aquaporin-1 (AQP1) were used to transduce the salivary glands of the Aec1/Aec2 mouse, which is recognized as a model for Sjögren's syndrome (Nguyen et al Scand J Immunol 2006 September; 64(3):

295-307). Mice in this study had established disease (30 weeks of age). AAV vectors expressing AQP-1 were transfected into the salivary glands of mice as described in Example 4 and the mice monitored for changes in salivary and lacrimal gland activity. The results of this analysis are shown in FIG. 5.

Figure 5A:
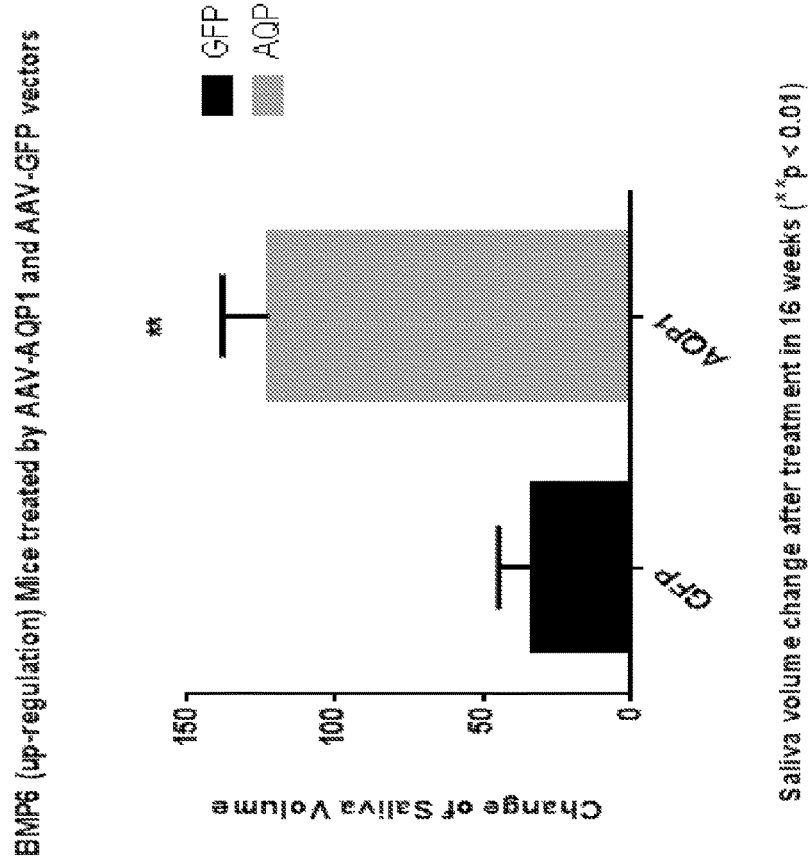
FIG. 5. Effect of AQP-1 on saliva and tear flow in a mouse model of Sjögren's Syndrome A). Change in pilocarpine stimulated saliva flow in Aec1/Aec2 mice treated with AAV2-AQP1 compared with GFP controls; B) Change in pilocarpine stimulated tear flow in Aec1/Aec2 mice treated with AAV2-AQP1 compared with GFP controls.
Figure 5B:
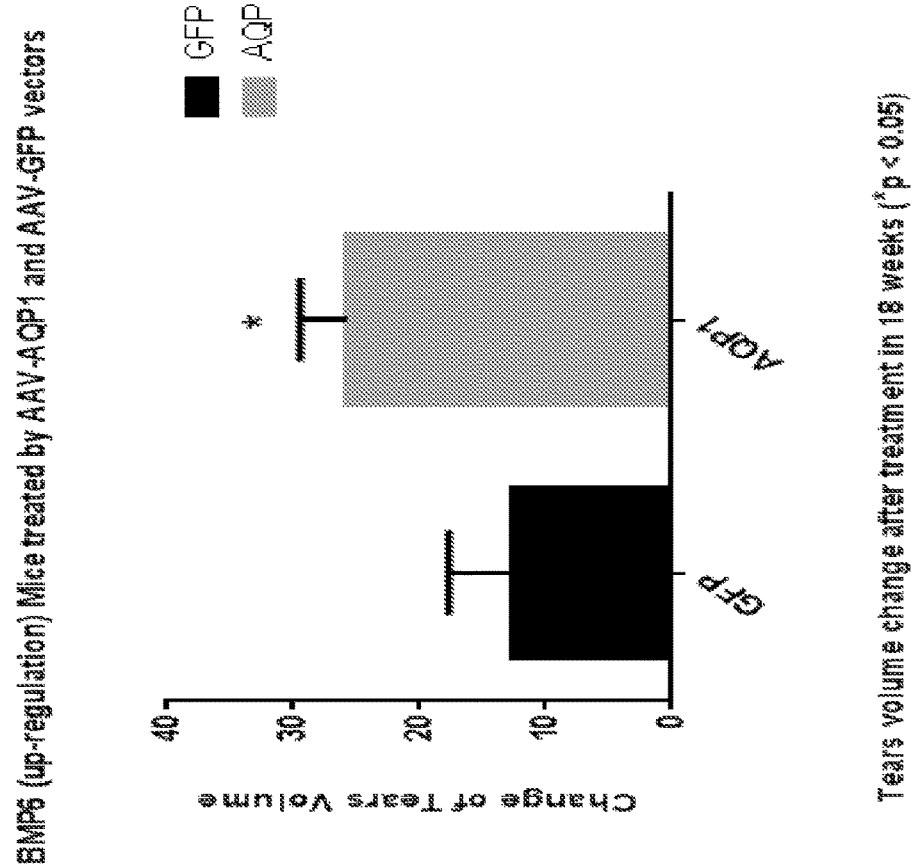

The results show that salivary gland activity increased by 4 weeks post cannulation of the vector and persisted till the end of the study (18 weeks post cannulation) (FIG. 5A). The results also showed an increase in lacrimal gland activity, indicating that the localized therapy in the salivary gland was able to initiate a systemic effect (FIG. 5B).

Because the loss of gland activity in the Aec1/Aec2 mouse is believed to be the result of inflammation in the tissue, salivary gland tissue from the transfected mice was analyzed for pro inflammatory cytokines such as gamma interferon. The results showed a decrease in B and T cells as well as gamma interferon producing, proinflammatory cytokine T-cells, suggesting that expression of AQP1 in the epithelial cells is able to reduce the inflammation seen in the gland, which likely has an effect on distal tissue secretory activity.

In summary, the data provided herein demonstrate that administration of AQP-1 to salivary gland cells can improve secretory activity associated with Sjögren's syndrome and produce a systemic effect as well.

While the present invention has been described with reference to the specific invention thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims.

What is claimed is:

1. A method to treat Sjögren's syndrome-associated xerostomia or xeropthalmia in a subject, comprising administering to the salivary gland or the lachrymal gland of the subject, an AAV vector that encodes an aquaporin-1 (AQP-1) protein.

2. The method of claim 1, wherein the AQP-1 protein is selected from the group consisting of:

a) an AQP-1 protein comprises at least a portion of an amino acid sequence selected from the group consisting of SEQ ID NO:2, SEQ ID NO:5, SEQ ID NO:8, SEQ ID NO:11 and SEQ ID NO:14, wherein the protein is able to form a channel that allows the passage of water; and, b) an AQP-1 protein comprising an amino acid sequence at least 80% identical to a sequence selected from the group consisting of SEQ ID NO:2, SEQ ID NO:5, SEQ ID NO:8, SEQ ID NO:11 and SEQ ID NO:14, wherein the protein is able to form a channel that allows the passage of water.

3. The method of claim 1, wherein the AQP-1 protein comprises the amino acid sequence selected from the group consisting of SEQ ID NO:2, SEQ ID NO:5, SEQ ID NO:8, SEQ ID NO:11 and SEQ ID NO:14.

4. The method of claim 1, wherein the AAV vector has a nucleic acid sequence at least 90% identical to SEQ ID NO:16 or SEQ ID NO:18.

5. The method of claim 1, wherein administration of the vector maintains or improves the level of salivary gland function relative to the level of salivary gland function prior to administration of the vector.

6. The method of claim 1, wherein administration of the vector maintains or improves the level of lachrymal gland function relative to the level of lachrymal gland function prior to administration of the vector.

7. The method of claim 1, wherein the AAV vector is administered as a virion comprising the AAV vector.

8. The method of claim 7, wherein the virion is an AAV virion.

\* \* \* \* \*